(12) United States Patent
Shibata et al.

(10) Patent No.: US 6,492,404 B1
(45) Date of Patent: Dec. 10, 2002

(54) THIAZOLYLCINNAMONITRILES AND PEST CONTROLLING AGENTS

(75) Inventors: Yasushi Shibata, Kawasaki (JP); Koichiro Aoyagi, Gainesville, FL (US); Hidemitsu Takahashi, Odawara (JP); Takao Iwasa, Odawara (JP); Tomohiro Take, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/763,478

(22) PCT Filed: Sep. 16, 1999

(86) PCT No.: PCT/JP99/05036

§ 371 (c)(1), (2), (4) Date: Feb. 20, 2001

(87) PCT Pub. No.: WO00/17174

PCT Pub. Date: Mar. 30, 2000

(30) Foreign Application Priority Data

Sep. 17, 1998 (JP) .......... 10-263323
Jan. 5, 1999 (JP) .......... 11-000717

(51) Int. Cl.⁷ .......... C07D 277/30; A01N 43/78
(52) U.S. Cl. .......... 514/365; 546/280; 548/204; 548/205
(58) Field of Search .......... 548/204, 205; 514/365; 546/280

(56) References Cited

U.S. PATENT DOCUMENTS 5,603,755 A * 2/1997 Okada .......... 514/365

* cited by examiner

*Primary Examiner*—Robert Gerstl
(74) *Attorney, Agent, or Firm*—Dennis G. LaPointe; Mason & Assoc., PA

(57) ABSTRACT

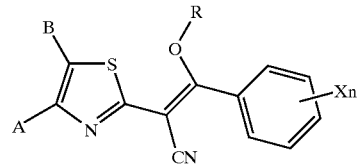

(1)

Compounds represented by the general formula (1); and pest controlling agents containing one or more of the compounds as the active ingredients, wherein A is substituted phenyl, $C_1$–$C_6$ alkly or the like; B is hydrogen, optionally substituted phenyl or the like; R is $C_1$–$C_6$ alkly, a group represented by the general formula: $COR^1$ (wherein $R^1$ is $C_1$–$C_{12}$ alkyl, $C_1$–$C_6$ alkoxy, $C_1$–$C_6$ haloalkyl or the like) or the like; X is halogeno, $C_1$–$C_6$ alkyl, $C_1$–$C_6$ haloalkyl or the like; and n is an integer of 1 to 5.

2 Claims, No Drawings

THIAZOLYLCINNAMONITRILES AND PEST CONTROLLING AGENTS

FIELD OF INVENTION

The present invention relates to novel thiazolylcinnamonitriles and pest controlling agents containing the said compounds as active ingredients.

BACKGROUND ART

A large number of pest controlling agents, such as insecticides and acaricides, have been used so far. However, many of them are hardly satisfactory as controlling agents because of insufficient efficacy, restrictions on their use due to drug resistance problems, phytotoxicity or pollution on plants, or strong toxicity on humans, domestic animals and fish. Therefore, there has been a desire for the development of agents applicable safely and having less of the drawbacks mentioned above.

As for cinnamonitrile derivatives similar to the compounds of the present invention, for example, 3-hydroxy-2-(4-phenyl-2-thiazolyl)-cinnamonitriles are disclosed in Japanese Patent Laid-open No. Sho 53-92769, Japanese Patent Laid-open No. Sho 55-154963 and EP 189960, and their alkali metal and ammonium salts in Japanese Patent Laid-open No. Sho 55-154962. However, none of them has been put to practical use as insecticides because of insufficient efficacy and other problems.

Further, WO 95/29591 and Japanese Patent Laid-open No. Hei 10-158254 have disclosed cinnamonitrile derivatives, similar to the compounds of the present invention, that are useful as anti-fouling agents for aquatic adhesive organisms. There are, however, no descriptions on their insecticidal activities.

DISCLOSURE OF THE INVENTION

It is an object of the present invention to provide pest controlling agents containing thiazolylcinnamonitriles as active ingredients, that have sure efficacy and can be used safely.

The present invention is directed to compounds represented by Formula (1)

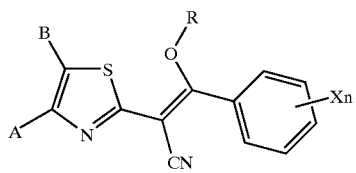

(1)

[wherein
  A is halogen, $C_{1-6}$ alkyl, $C_{1-6}$ haloalkyl, $C_{1-6}$ alkoxy, optionally substituted $C_{3-6}$ cycloalkyl, optionally substituted pyridyl, optionally substituted thienyl, substituted phenyl or optionally substituted phenoxy;
  B is hydrogen, halogen, $C_{1-6}$ alkoxycarbonyl, optionally substituted phenyl, $C_{1-6}$ alkyl, $C_{1-6}$ haloalkyl or $C_{3-6}$ cycloalkyl;
  R is $C_{1-6}$ alkyl, a group of Formula $COR^1$ (wherein $R^1$ is $C_{1-12}$ alkyl, $C_{1-6}$ haloalkyl, optionally substituted $C_{3-6}$ cycloalkyl, $C_{1-6}$ alkoxy, $C_{1-6}$ alkoxy $C_{1-6}$ alkyl, $C_{1-6}$ alkylthio $C_{1-6}$ alkyl, mono-$C_{1-6}$ alkylamino, di-$C_{1-6}$ alkylamino, optionally substituted phenyl $C_{1-6}$ alkyl, optionally substituted phenoxy $C_{1-6}$ alkyl, optionally substituted phenylthio $C_{1-6}$ alkyl or optionally substituted phenyl), or a group of Formula $SO_2R^2$ (wherein $R^2$ is $C_{1-6}$ alkyl or optionally substituted phenyl);
  X is cyano, nitro, halogen, $C_{1-6}$ alkyl, $C_{1-6}$ haloalkyl, $C_{1-6}$ alkoxy, $C_{1-6}$ haloalkoxy, optionally substituted phenyl or optionally substituted phenoxy; and
  n is an integer between 1 and 5], and pest controlling agents containing one or more of the said compounds as active ingredients.

In the above Formula (1),
  A is halogen such as fluorine, chlorine, bromine and iodine;
  $C_{1-6}$ alkyl such as methyl, ethyl, propyl, isopropyl, butyl, sec-butyl, isobutyl, t-butyl, pentyl and its isomers, and hexyl and its isomers;
  $C_{1-6}$ haloalkyl such as chloromethyl, fluoromethyl, bromomethyl, dichloromethyl, difluoromethyl, dibromomethyl, trichloromethyl, trifluoromethyl, tribromomethyl, trichloroethyl, trifluoroethyl and pentafluoroethyl;
  $C_{1-6}$ alkoxy such as methoxy, ethoxy, propoxy, isopropoxy, butoxy, sec-butoxy, isobutoxy and t-butoxy;
  optionally substituted $C_{3-6}$ cycloalkyl such as cyclopropyl, cyclopentyl, 1-methylcyclopentyl, cyclohexyl and 1-methylcyclohexyl;
  optionally substituted pyridyl, such as 2-pyridyl, 3-pyridyl and 4-pyridyl that may have substituents at arbitrary positions of the pyridine ring;
  thienyl, such as 2-thienyl and 3-thienyl 1 that may have substituents at arbitrary positions of the thiophene ring;
  phenyl having substituents at arbitrary positions of the benzene ring; or
  phenoxy having optional substituents at arbitrary positions of the benzene ring.

Examples of substituents of the aforementioned pyridyl, thienyl, phenyl and phenoxy groups include halogens such as fluorine and chlorine; $C_{1-6}$ alkyl such as methyl and ethyl; $C_{1-6}$ alkoxy such as methoxy, ethoxy and isopropoxy; and nitro. These pyridyl, thienyl, phenyl and phenoxy groups may have two or more, same or different, substituents.

B is hydrogen;
  halogen such as fluorine, chlorine, bromine and iodine;
  $C_{1-6}$ alkoxycarbonyl such as methoxycarbonyl, ethoxycarbonyl, propoxycarbonyl, isopropoxycarbonyl, butoxycarbonyl and t-butoxycarbonyl;
  $C_{1-6}$ alkyl such as methyl, ethyl, propyl, isopropyl, butyl, sec-butyl, isobutyl, t-butyl, pentyl and hexyl;
  $C_{1-6}$ haloalkyl such as chloromethyl, fluoromethyl, bromomethyl, dichloromethyl, difluoromethyl, dibromomethyl, trichloromethyl, trifluoromethyl, tribromomethyl, trichloroethyl, trifluoroethyl and pentafluoroethyl; or
  $C_{3-6}$ cycloalkyl such as cyclopropyl, cyclopentyl and cyclohexyl.

R is $C_{1-6}$ alkyl such as methyl, ethyl, propyl, isopropyl, butyl and t-butyl; or
  a group represented by Formula $COR^1$ or $SO_2R^2$,
  wherein $R^1$ is $C_{1-12}$ alkyl such as methyl, ethyl, propyl, isopropyl, butyl, isobutyl, s-butyl, t-butyl, pentyl and its isomers, hexyl and its isomers, heptyl and its isomers, nonyl and its isomers and dodecyl, and branched alkyl groups are particularly preferred;

$C_{1-6}$ haloalkyl such as chloromethyl, fluoromethyl, bromomethyl, dichloromethyl, difluoromethyl, dibromomethyl, trichloromethyl, trifluoromethyl, tribromomethyl, trichloroethyl, trifluoroethyl and pentafluoroethyl;

optionally substituted $C_{3-6}$ cycloalkyl such as cyclopropyl, 1-methylcyclopropyl, cyclopentyl, 1-methylcyclopentyl, cyclohexyl and 1-methylcyclohexyl;

$C_{1-6}$ alkoxy $C_{1-6}$ alkyl such as methoxymethyl, methoxyethyl, ethoxymethyl, propoxymethyl and butoxymethyl;

$C_{1-6}$ alkylthio $C_{1-6}$ alkyl such as methylthiomethyl, methylthioethyl, ethylthioethyl, ethylthiomethyl, propylthiomethyl and butylthiomethyl;

mono- or di-$C_{1-6}$ alkylamino such as methylamino, ethylamino, propylamino, dimethylamino, diethylamino, dipropylamino, dibutylamino and ethylisopropylamino;

optionally substituted phenyl $C_{1-6}$ alkyl, such as benzyl, phenethyl and phenylpropyl that may have substituents at arbitrary positions of the benzene ring;

optionally substituted phenoxy $C_{1-6}$ alkyl, such as phenoxymethyl and phenoxyethyl that may have substituents at arbitrary positions of the benzene ring;

optionally substituted phenylthio $C_{1-6}$ alkyl, such as phenylthiomethyl, phenylthioethyl, phenylthiopropyl and phenylthiobutyl that may have substituents at arbitrary positions of the benzene ring; or phenyl having optional substituents at arbitrary positions of the benzene ring.

$R^2$ is $C_{1-6}$ alkyl such as methyl, ethyl, propyl, isopropyl, butyl, isobutyl, s-butyl, t-butyl, pentyl and its isomers, and hexyl and its isomers, or phenyl having optional substituents at arbitrary positions of the benzene ring.

In these $R^1$ and $R^2$, examples of benzene-ring substituents of the phenyl $C_{1-6}$ alkyl, phenylthio $C_{1-6}$ alkyl, phenoxy $C_{1-6}$ alkyl and phenyl groups include halogen such as fluorine and chlorine, $C_{1-6}$ alkyl such as methyl and ethyl, $C_{1-6}$ alkoxy such as methoxy, ethoxy and isopropoxy, and nitro. These benzene rings may have two or more, same or different, substituents.

X is cyano, nitro, halogen such as chlorine, bromine and fluorine;

$C_{1-6}$ alkyl such as methyl, ethyl, propyl, isopropyl, butyl, isobutyl, s-butyl, t-butyl, pentyl and its isomers, and hexyl and its isomers;

$C_{1-6}$ haloalkyl such as chloromethyl, fluoromethyl, dichloromethyl, trichloromethyl, trifluoromethyl, 1-fluoroethyl, 2,2-difluoroethyl, 2,2,2-trifluoroethyl and pentafluoroethyl;

$C_{1-6}$ alkoxy such as methoxy, ethoxy, propoxy, isopropoxy and butoxy;

$C_{1-6}$ haloalkoxy such as chloromethoxy, dichloromethoxy, trichloromethoxy, trifluoromethoxy, 1-fluoroethoxy and 1,1-difluoroethoxy;

optionally substituted phenyl, or optionally substituted phenoxy.

Examples of substituents of these phenyl and phenoxy groups include halogen such as fluorine and chlorine; $C_{1-6}$ alkyl such as methyl and ethyl; $C_{1-6}$ alkoxy such as methoxy, ethoxy and isopropoxy; and nitro. The said phenyl group may have two or more, same or different, substituents.

When n is 2 or larger, X's may be the same or different groups.

Compounds having particularly excellent pest controlling effects among the compounds of the present invention, compared to similar, known cinnamonitrile compounds, are those where, in the above Formula (1), A is $C_{1-6}$ alkyl, optionally substituted $C_{3-6}$ cycloalkyl, optionally substituted pyridyl, optionally substituted thienyl or substituted phenyl; B is hydrogen; R is $COR^1$ or $SO_2R^2$; and X is halogen, $C_{1-6}$ alkyl, $C_{1-6}$ haloalkyl or $C_{1-6}$ alkoxy, and at least one of the substituents is at position 2.

FORMS TO IMPLEMENT THE INVENTION

The compounds of the present invention are prepared, for example, according to the following:

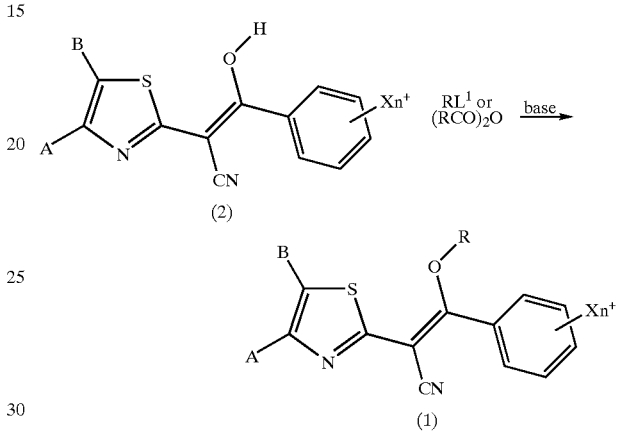

(wherein A, B, R, X and n are as defined above, and $L^1$ is a leaving group such as halogen, $C_{1-6}$ alkoxy, phenoxy, 1-imidazolyl, 1-pyrazolyl, p-toluenesulfonyloxy, methanesulfonyloxy or trifluoromethanesulfonyloxy).

That is, 1 mole of a compound of Formula (2) is reacted with 0.5 to 2 moles of a compound of Formula (3) in an inert solvent in the presence of a base, to give a compound of Formula (1).

Examples of bases used for this reaction include alkali metal hydroxides such as sodium hydroxide and potassium hydroxide; carbonates such as sodium carbonate and potassium carbonate; organic metals such as n-butyl lithium and lithium diisopropylamide (LDA); and organic bases such as triethylamine, diisopropylethylamine and pyridine.

Solvents able to be used include N,N-dimethylformamide (DMF), dimethylsulfoxide (DMSO), tetrahydrofuran (THF), acetonitrile, hexamethylphosphoramide (HMPT), benzene, toluene, dichloromethane, chloroform and carbon tetrachloride. Preferred reaction temperatures are from −78° C. to the boiling point of solvents used.

The compounds of Formula (1) of the present invention have 2 stereoisomers. One of the isomers or a mixture of the isomers may be produced, depending on reaction conditions and purification methods. These isomers are all covered by the present invention.

A compound of Formula (2) of a starting material can be prepared as follows:

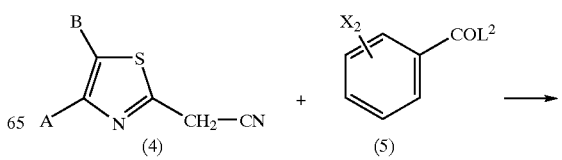

-continued (wherein A, B, X and n are as defined above, and $L^2$ is a leaving group such as halogen, $C_{1-6}$ alkoxy, phenoxy, 1-imidazolyl or 1-pyrazolyl).

That is, 1 mole of a compound of Formula (4) is reacted with 0.5 to 2 moles of a compound of Formula (5) in an inert solvent in the presence of a base, to give a compound of Formula (2).

Examples of bases used for this reaction include alkali metal hydroxides such as sodium hydroxide and potassium hydroxide; carbonates such as sodium carbonate and potassium carbonate; organic metals such as n-butyl lithium and LDA; and organic bases such as triethylamine, diisopropylethylamine and pyridine.

Solvents able to be used include DMF, DMSO, THF, acetonitrile, hexamethylphosphoramide (HMPT), benzene, toluene, dichloromethane, chloroform and carbon tetrachloride. Preferred reaction temperatures are from −78° C. to the boiling point of solvents used.

A target compound is obtained with usual post-treatments after the completion of the reaction.

The structures of the compounds of the present invention were determined by IR, MNR, MS and other means.

Representative examples of the compounds of the present invention, that can be prepared according to the above processes, are shown in Tables 1 to 4. The symbols used in the tables have the following meanings:

Me: methyl, Et: ethyl, Pr: propyl, Bu: butyl, Pen: pentyl, Hex: hexyl, Ph: phenyl, n: normal, i: iso, t: tertiary, neo: neo, and c: cyclo R1: [structure: C(=O)C(Me)(Me)Et]

R2: [structure: C(=O)C(Me)(Me)nPr]

R3: [structure: C(=O)C(Me)(Me)nBu]

R4: [structure: C(=O)C(Me)(Me)nPen]

R5: [structure: C(=O)C(Me)(Me)nHex]

R6: [structure: C(=O)C(Me)(Me)CH₂Ph]

R7: [structure: C(=O)C(Me)(Me)CH₂CH₂Ph]

R8: [structure: C(=O)C(Me)(Me)CH₂CF₃]

R9: [structure: C(=O)C(Me)(Me)CH₂CH₂F]

R10: [structure: C(=O)C(Me)(Me)CH₂CH₂Cl]

R11: [structure: C(=O)C(Me)(Me)CH₂CH₂OMe]

R12: [structure: C(=O)-nC₁₂H₂₅]

R13: [structure: C(=O)CH₂OMe]

R14: [structure: C(=O)CH₂OPh]

R15: [structure: C(=O)CH₂SMe]

R16: [structure: C(=O)CH₂SPh]

-continued
R17: 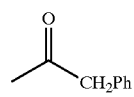
R18: 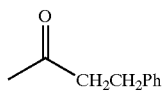
R19: 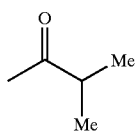
R20: 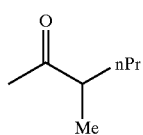
R21: 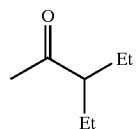
R22: 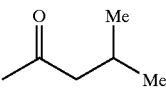
R23: 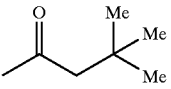
R24: 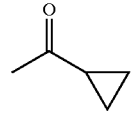
R25: 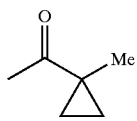
R26: 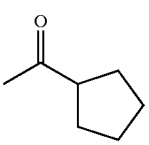
R27: 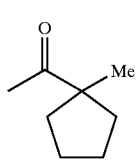
-continued
R28: 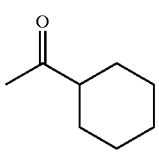
R29: 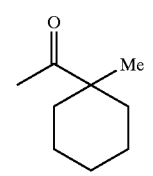
R30: 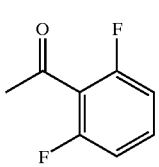
R31: 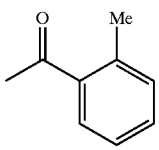
R32: 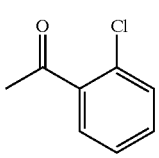
R33: 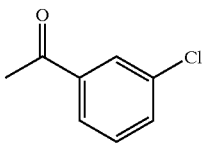
R34: 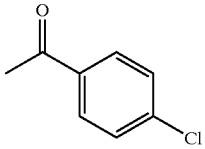
R35: 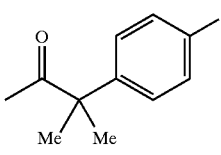
R36: 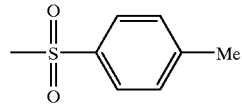

TABLE 1
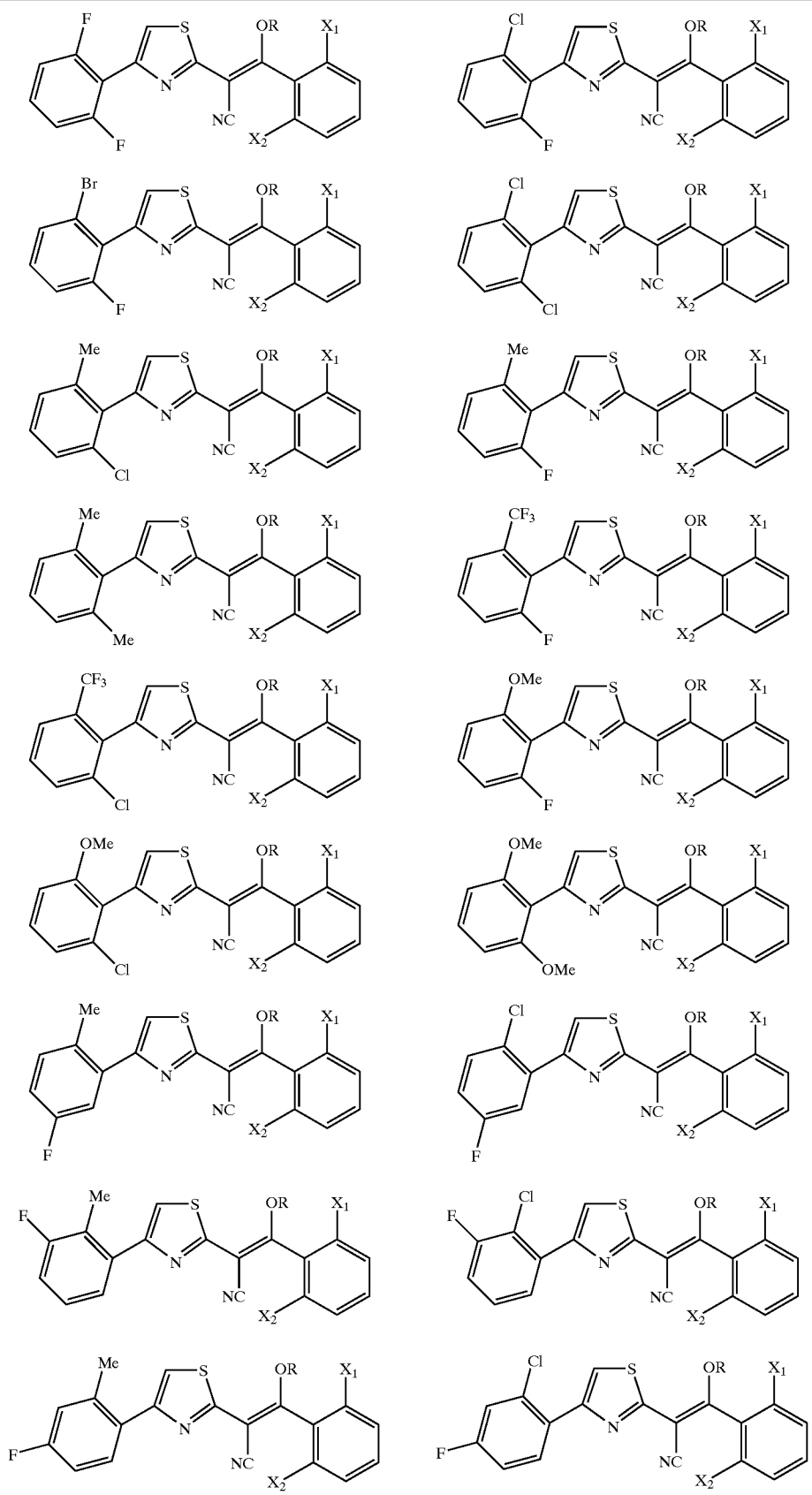

TABLE 1-continued
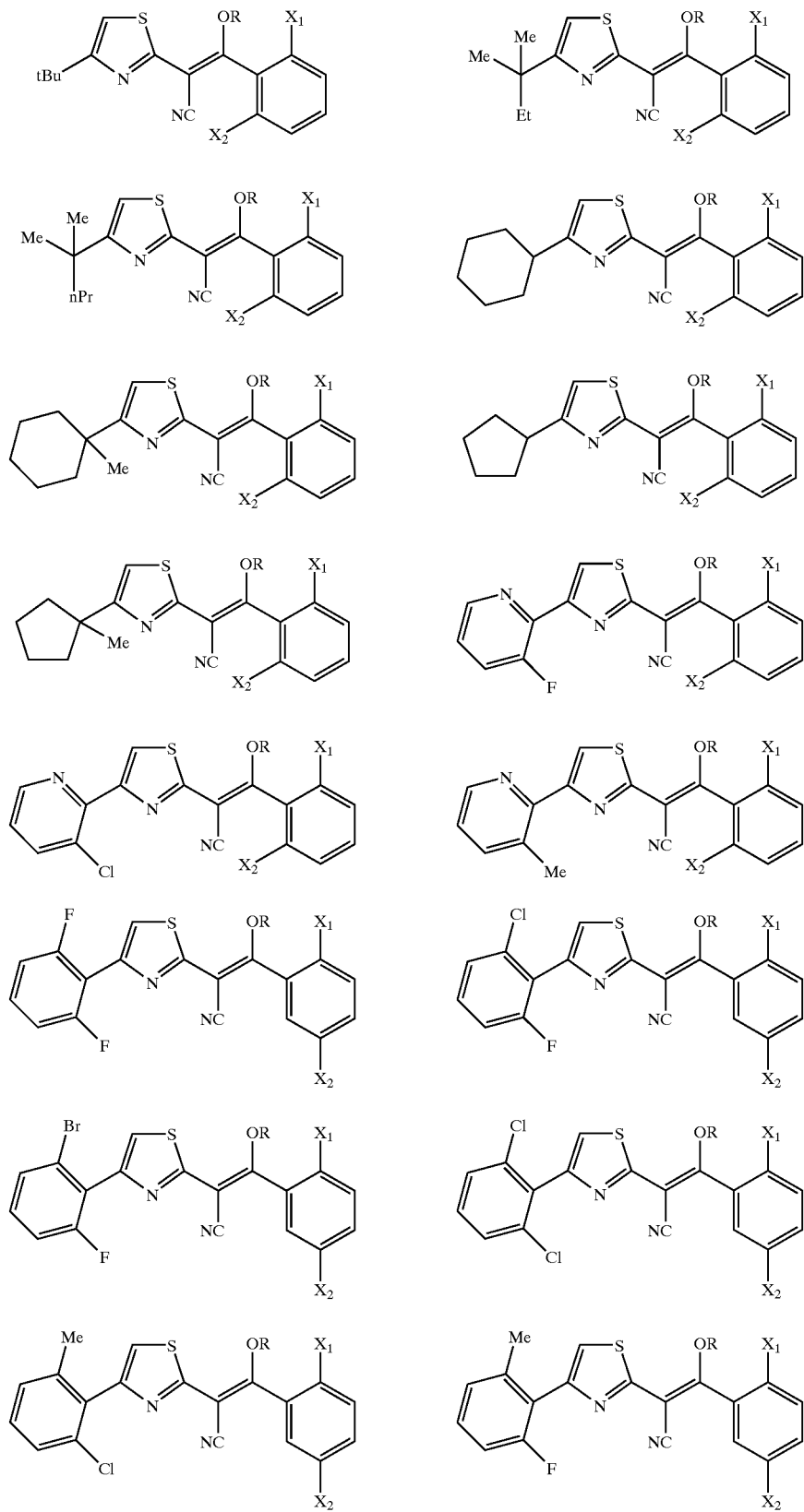

TABLE 1-continued
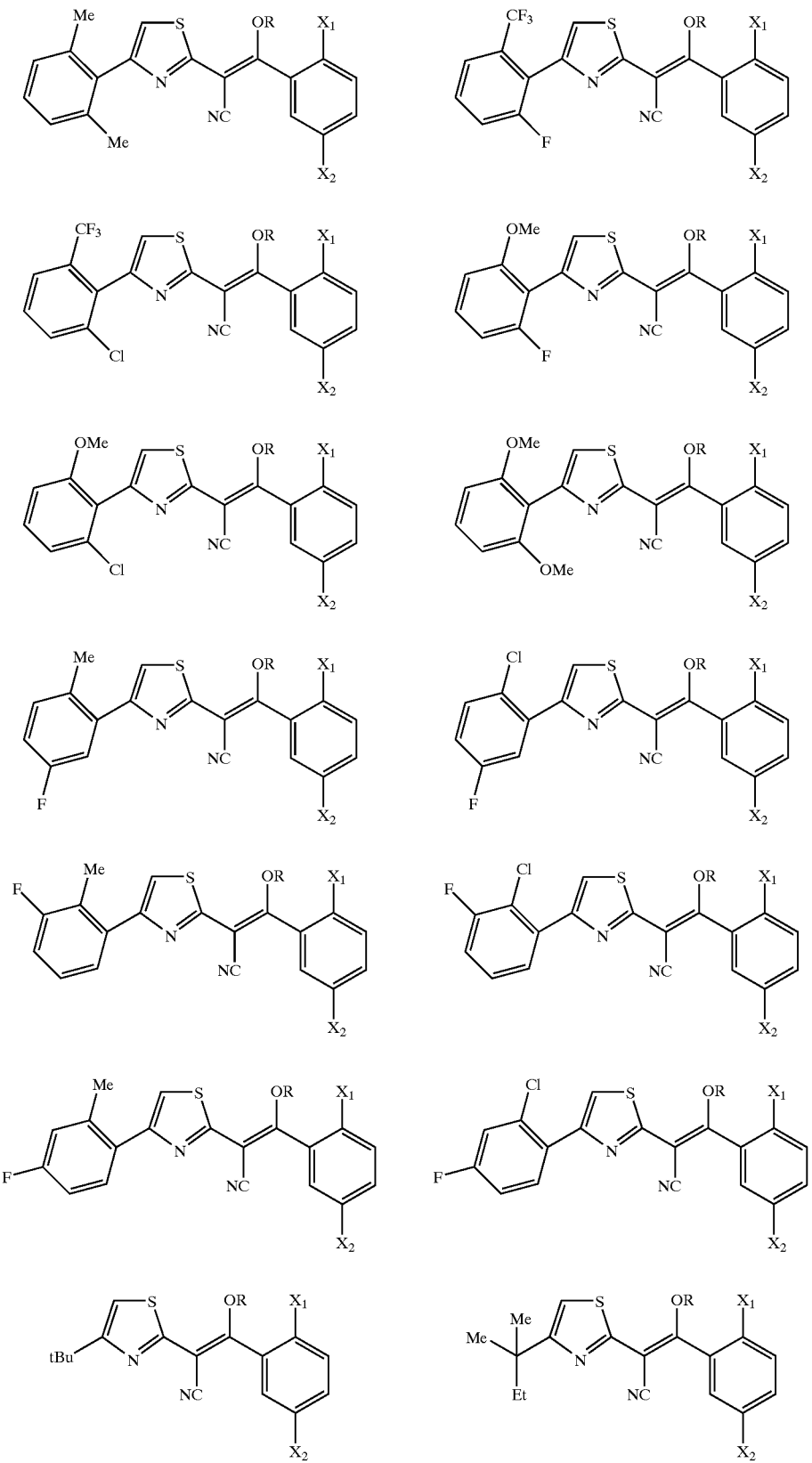

TABLE 1-continued
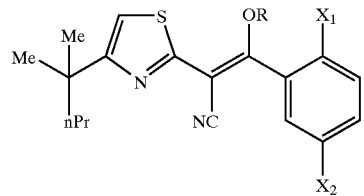 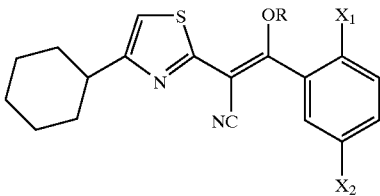
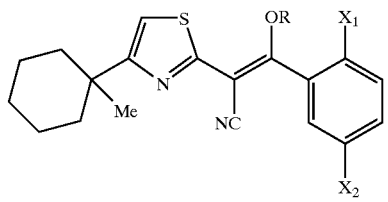 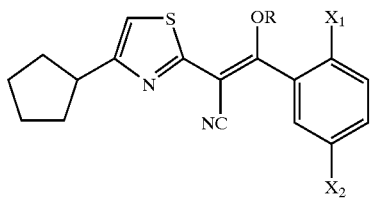
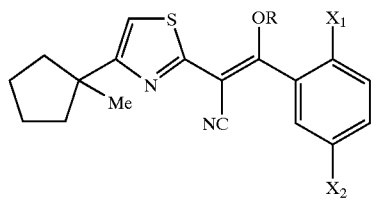 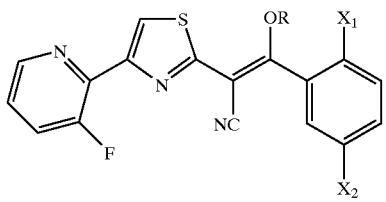
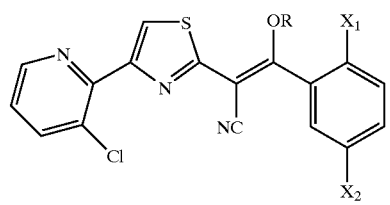 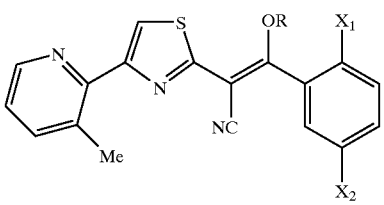
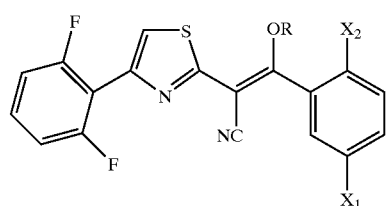 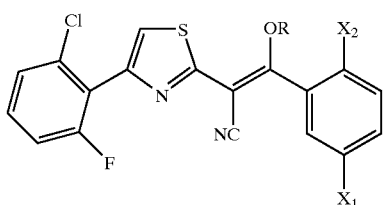
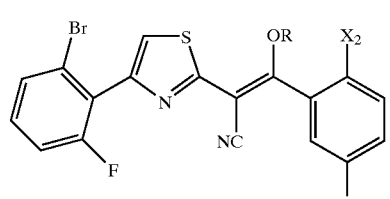 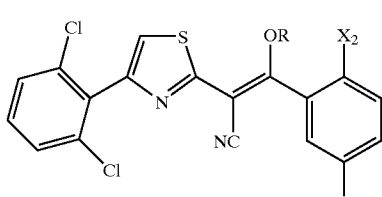
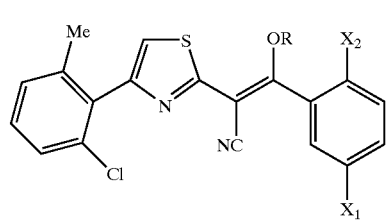

TABLE 1-continued
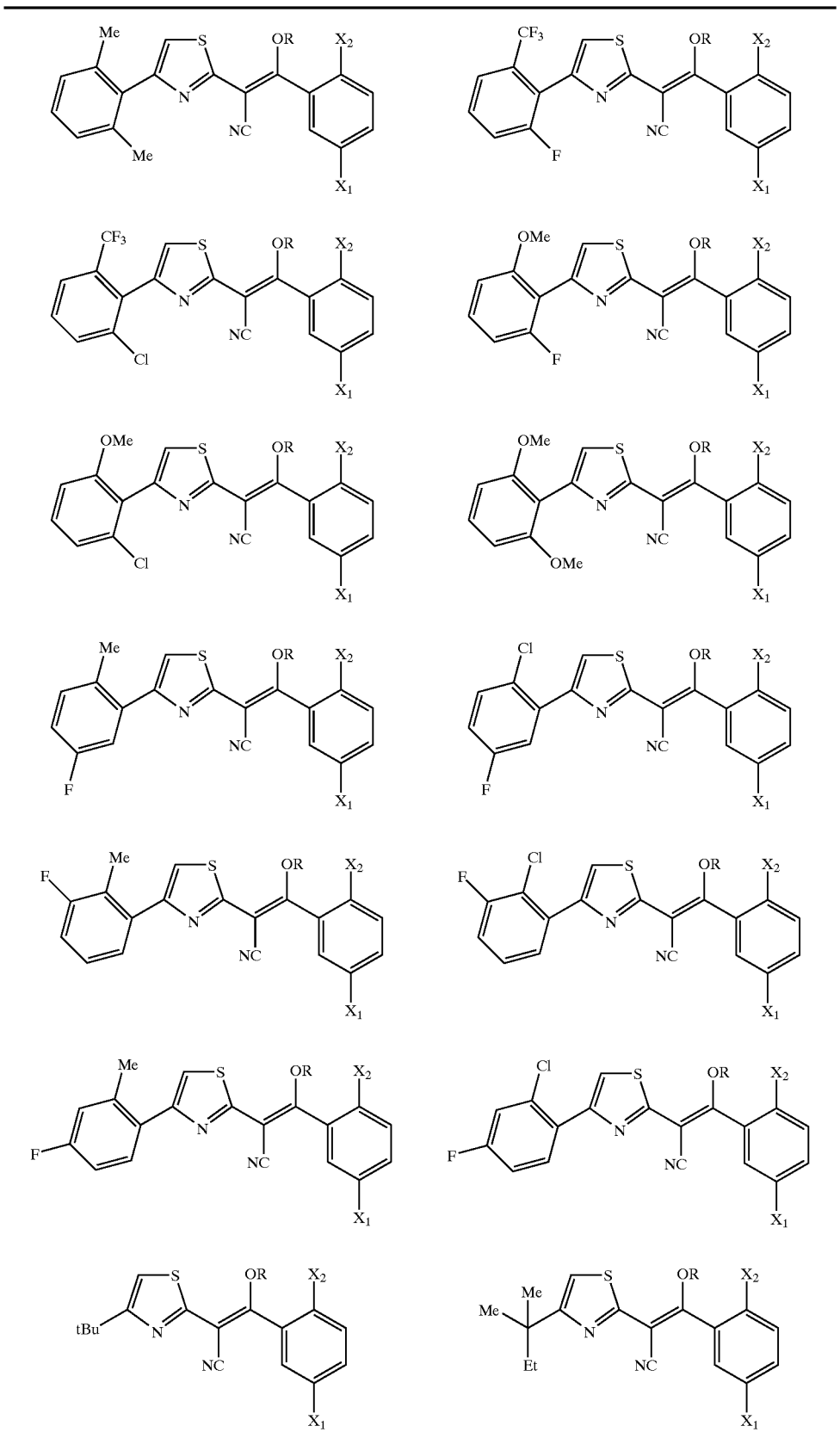

TABLE 1-continued
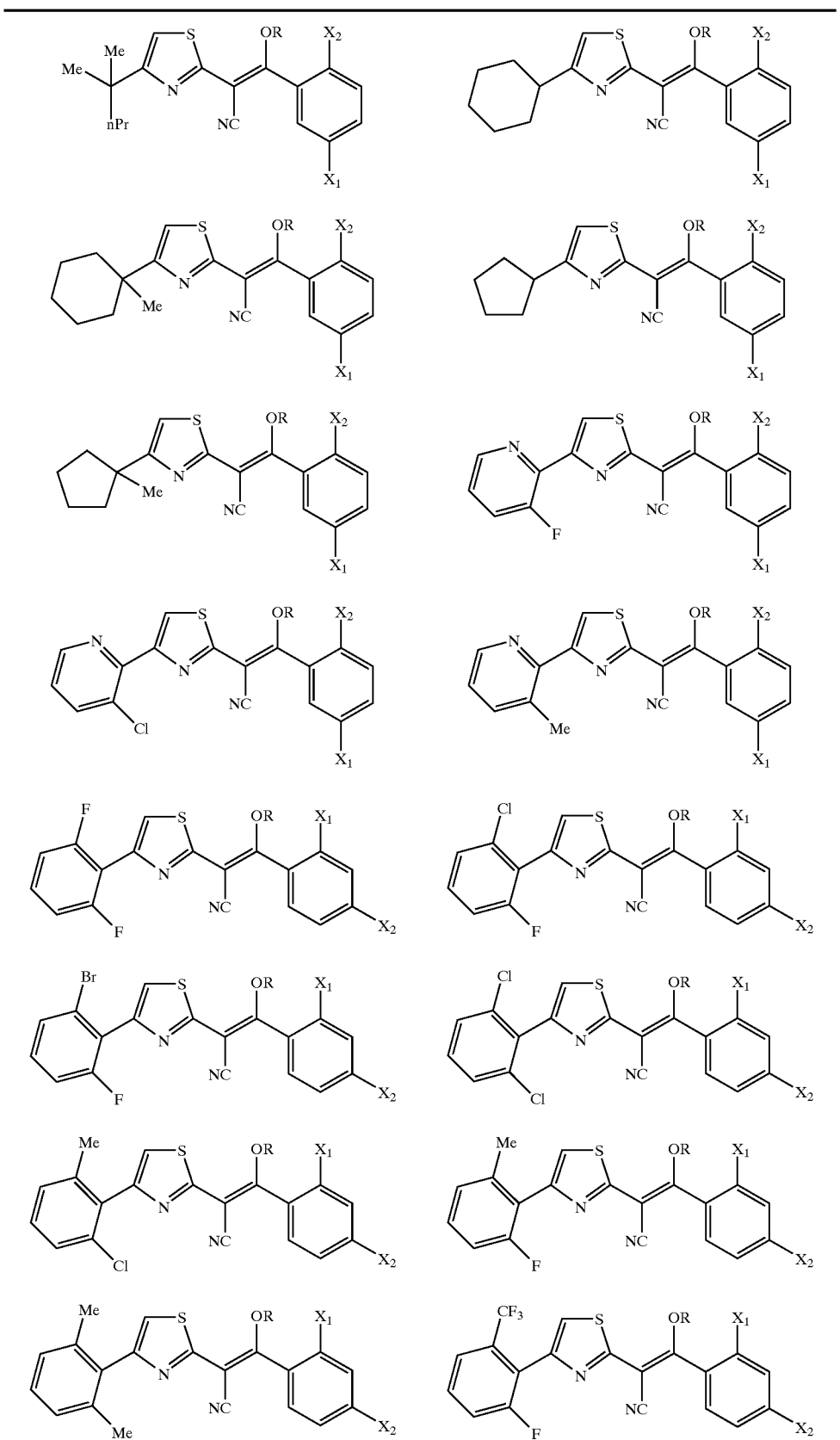

TABLE 1-continued
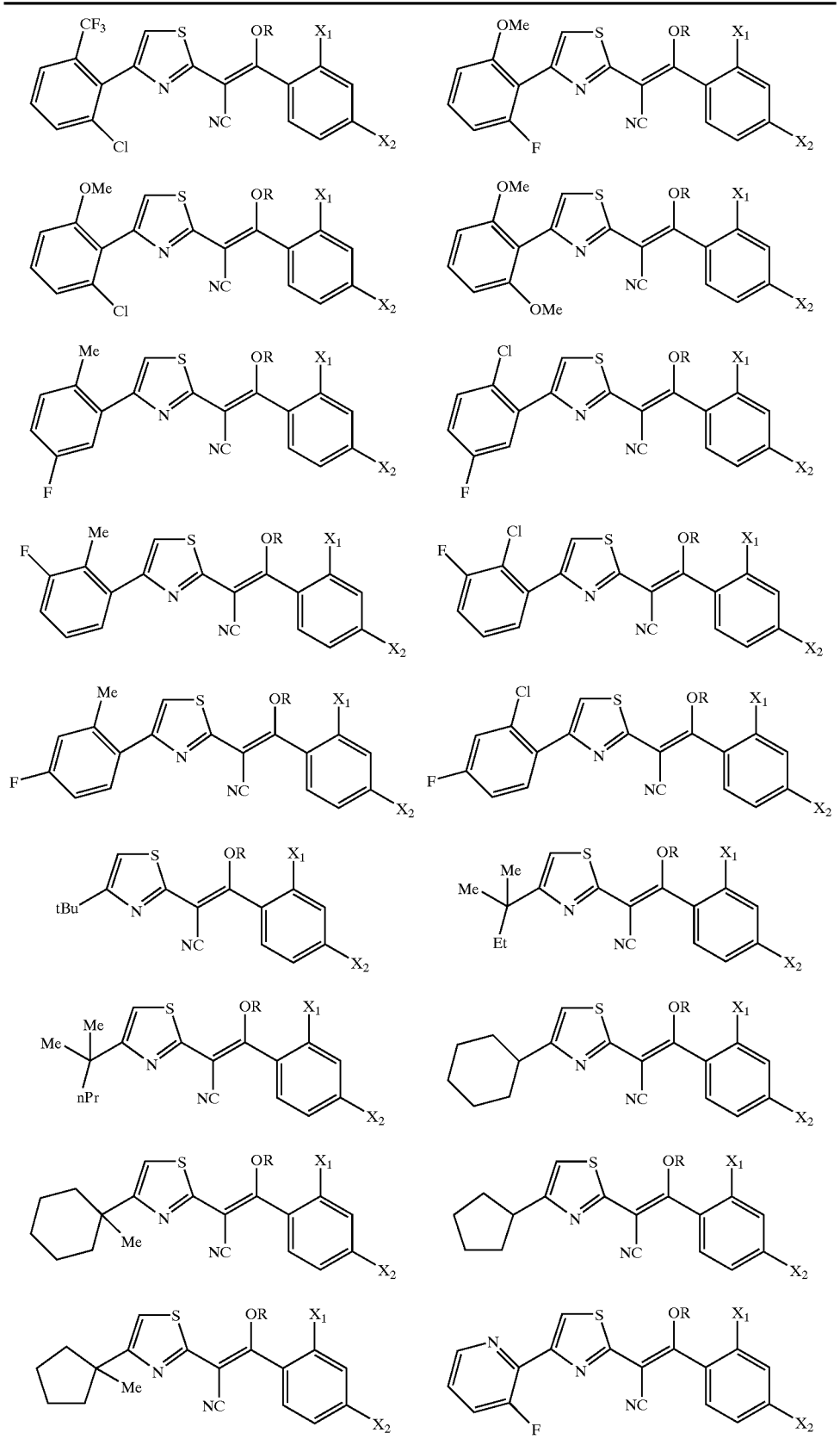

TABLE 1-continued
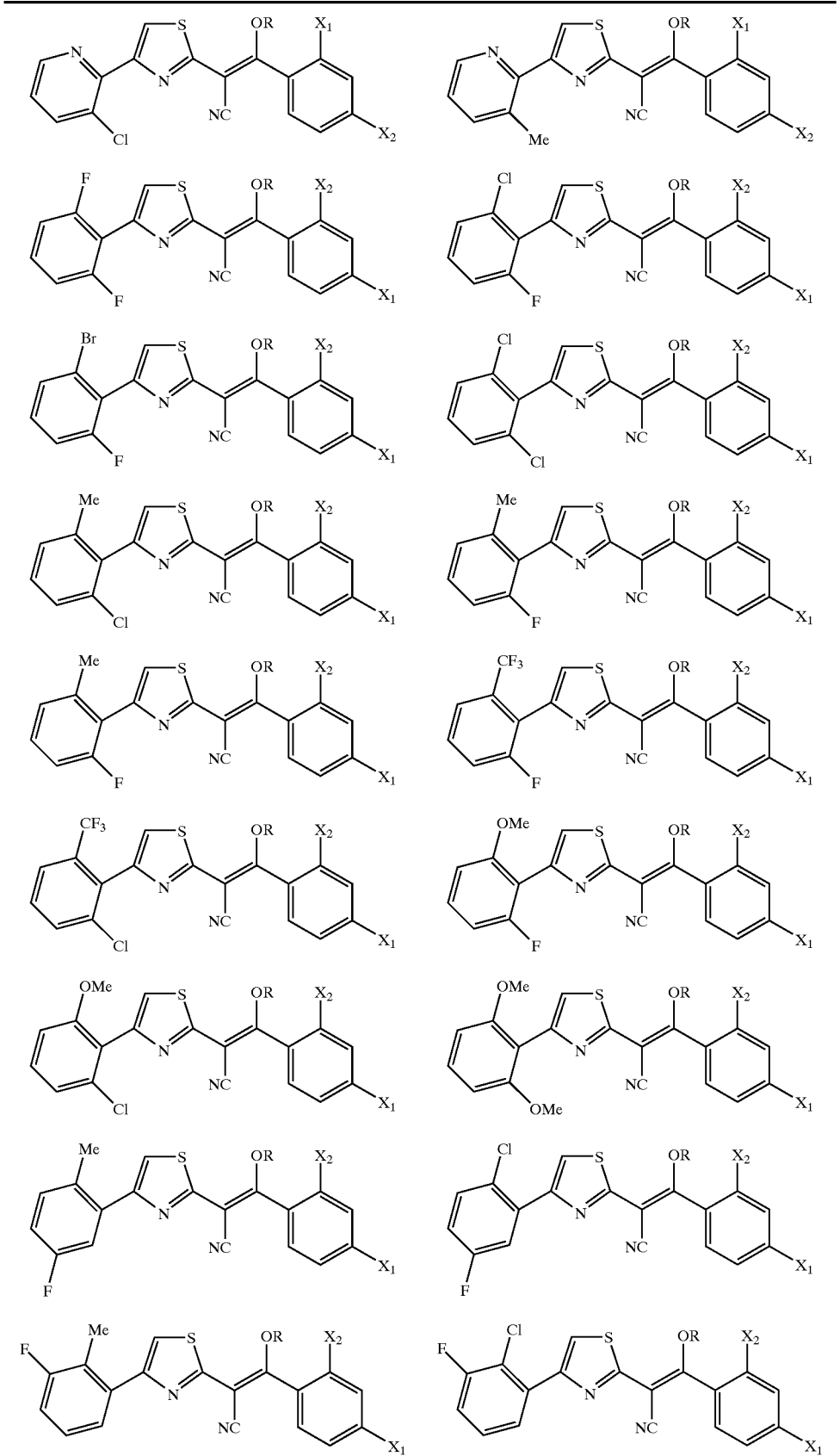

TABLE 1-continued
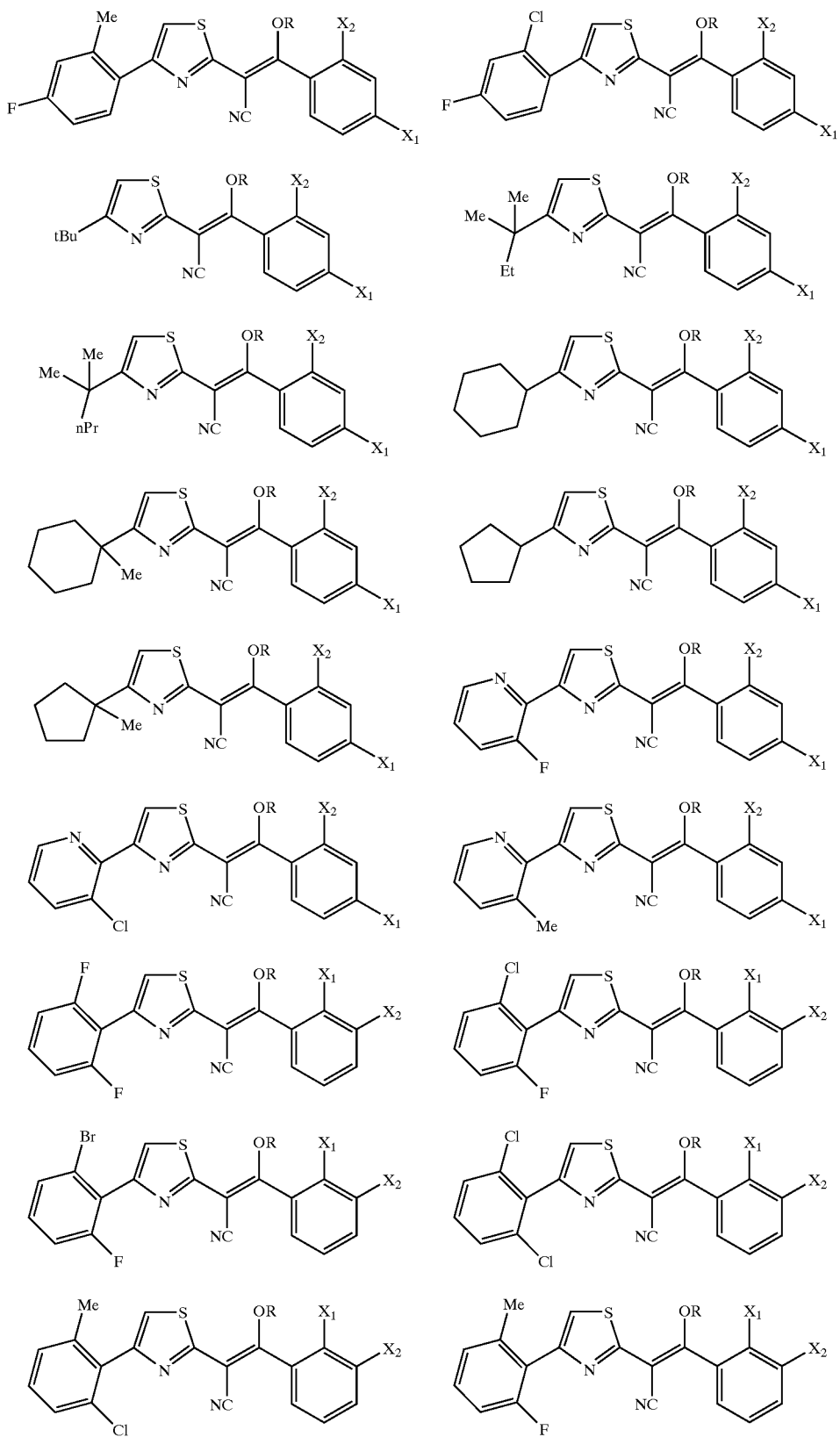

TABLE 1-continued
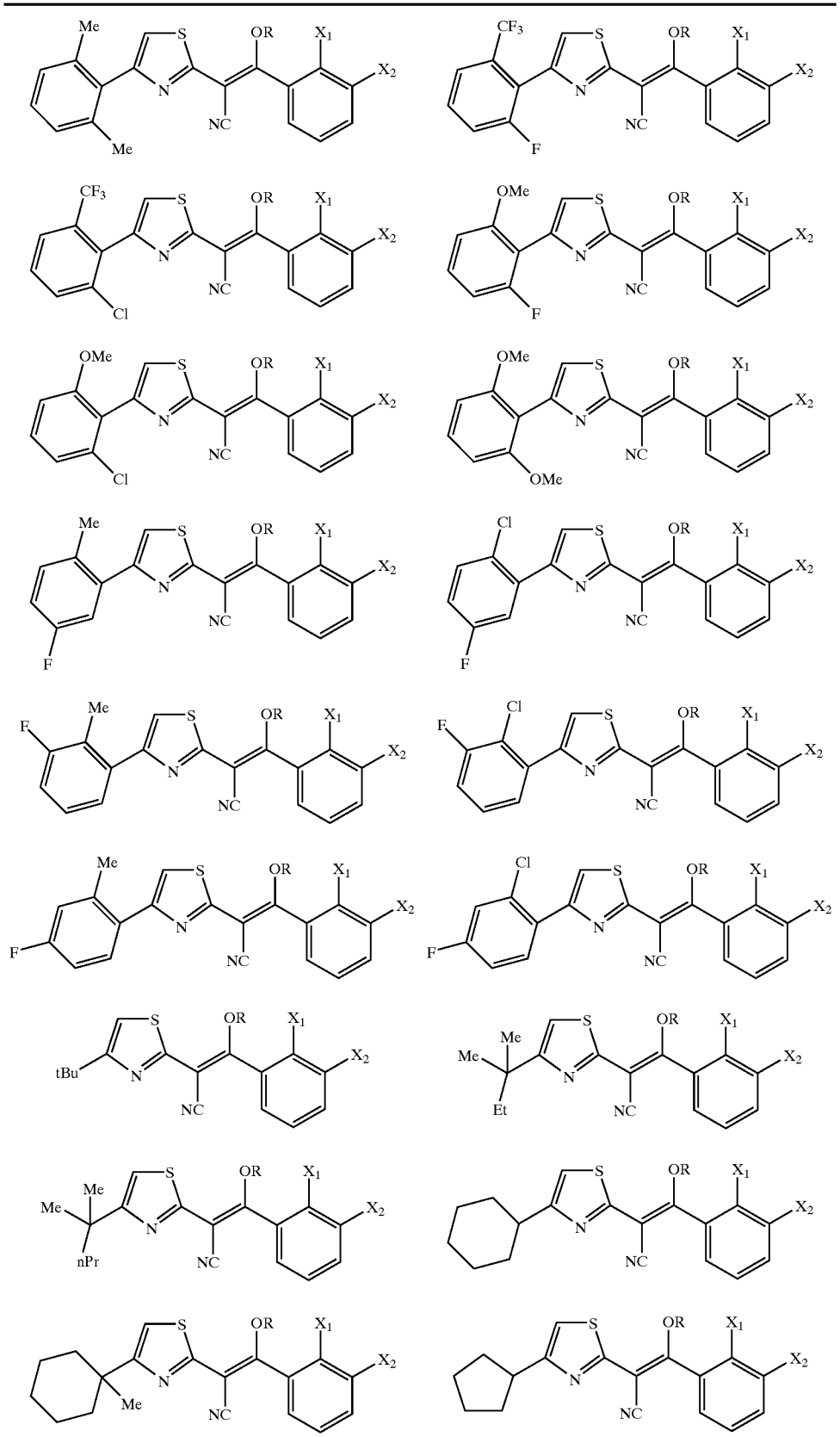

TABLE 1-continued
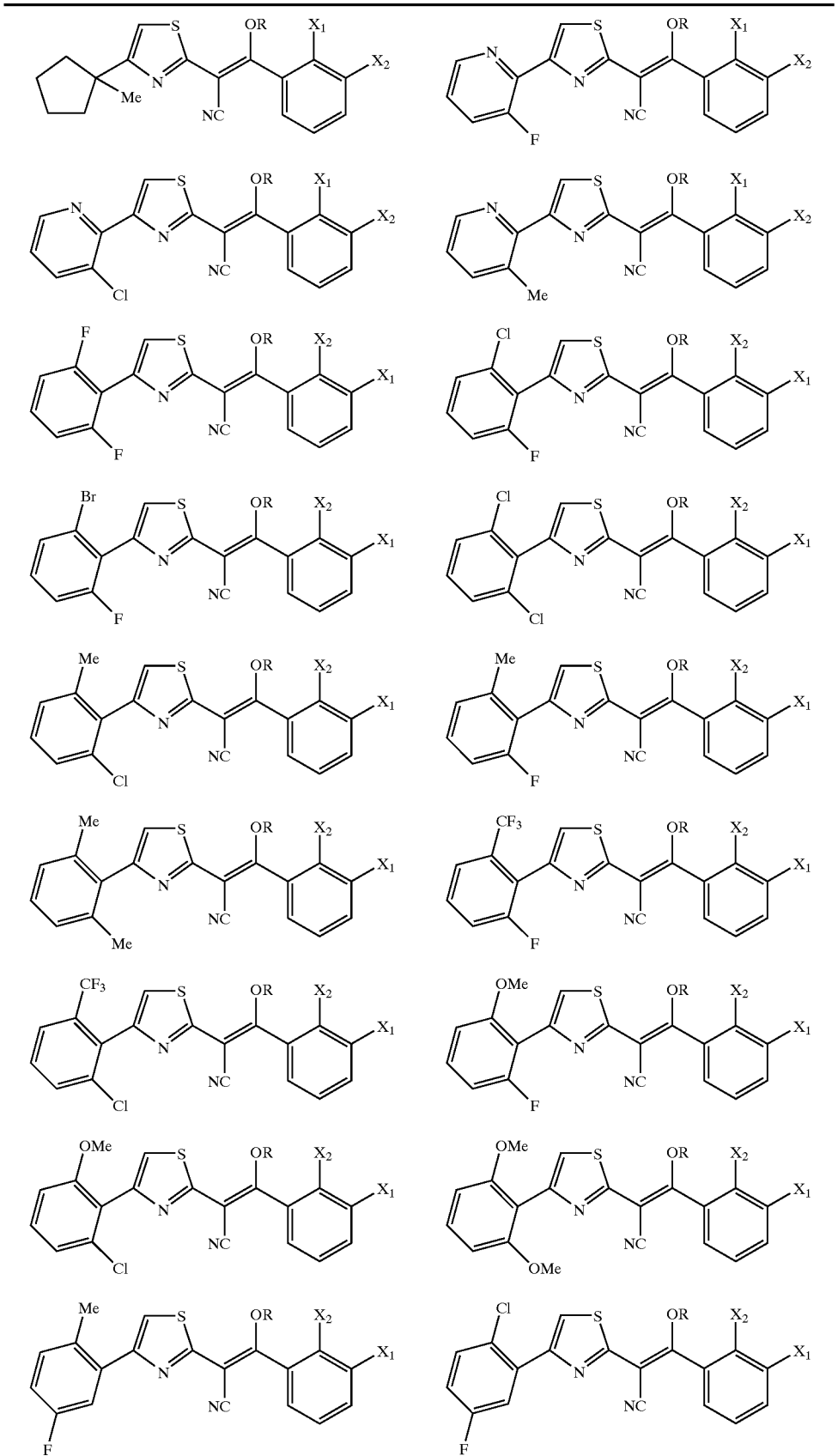

TABLE 1-continued

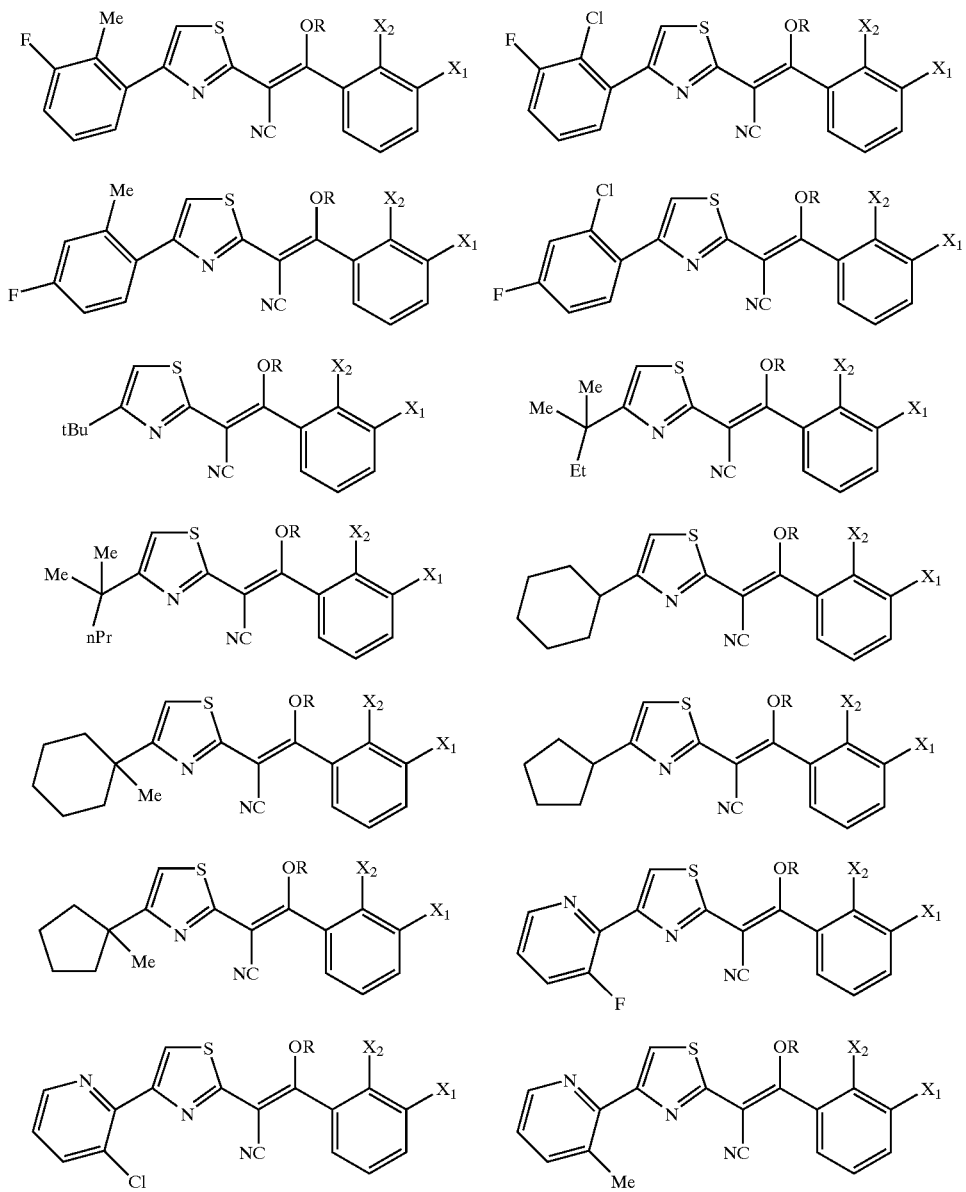

| X₁ | X₂ | R | X₁ | X₂ | R | X₁ | X₂ | R | X₁ | X₂ | R |
|---|---|---|---|---|---|---|---|---|---|---|---|
| CF₃ | H | COtBu | CF₃ | H | R21 | Me | H | CO₂CH₂Ph | Me | H | R31 |
| CF₃ | H | COMe | CF₃ | H | R22 | Me | H | CONMe₂ | Me | H | R32 |
| CF₃ | H | COEt | CF₃ | H | R23 | Me | H | R1 | Me | H | R33 |
| CF₃ | H | COnPr | CF₃ | H | R24 | Me | H | R2 | Me | H | R34 |
| CF₃ | H | COnBu | CF₃ | H | R25 | Me | H | R3 | Me | H | R35 |
| CF₃ | H | COPh | CF₃ | H | R26 | Me | H | R4 | Me | H | Me |
| CF₃ | H | COCCl₃ | CF₃ | H | R27 | Me | H | R5 | Me | H | CH₃Ph |
| CF₃ | H | COCF₃ | CF₃ | H | R28 | Me | H | R6 | Me | H | SO₂Me |
| CF₃ | H | CO₂Me | CF₃ | H | R29 | Me | H | R7 | Me | H | SO₂Et |
| CF₃ | H | CO₂nBu | CF₃ | H | R30 | Me | H | R8 | Me | H | SO₂nPr |
| CF₃ | H | CO₂CH₂Ph | CF₃ | H | R31 | Me | H | R9 | Me | H | SO₂iPr |
| CF₃ | H | CONMe₂ | CF₃ | H | R32 | Me | H | R10 | Me | H | R36 |
| CF₃ | H | R1 | CF₃ | H | R33 | Me | H | R11 | Cl | H | COtBu |
| CF₃ | H | R2 | CF₃ | H | R34 | Me | H | R12 | Cl | H | COMe |
| CF₃ | H | R3 | CF₃ | H | R35 | Me | H | R13 | Cl | H | COEt |
| CF₃ | H | R4 | CF₃ | H | Me | Me | H | R14 | Cl | H | COnPr |
| CF₃ | H | R5 | CF₃ | H | CH₂Ph | Me | H | R15 | Cl | H | COnBu |
| CF₃ | H | R6 | CF₃ | H | SO₂Me | Me | H | R16 | Cl | H | COPh |
| CF₃ | H | R7 | CF₃ | H | SO₂Et | Me | H | R17 | Cl | H | COCCl₃ |

TABLE 1-continued

| | | | | | | | | | | | |
|---|---|---|---|---|---|---|---|---|---|---|---|
| CF₃ | H | R8 | CF₃ | H | SO₂nPr | Me | H | R18 | Cl | H | COCF₃ |
| CF₃ | H | R9 | CF₃ | H | SO₂iPr | Me | H | R19 | Cl | H | CO₂Me |
| CF₃ | H | R10 | CF₃ | H | R36 | Me | H | R20 | Cl | H | CO₂nBu |
| CF₃ | H | R11 | Me | H | COtBu | Me | H | R21 | Cl | H | CO₂CH₂Ph |
| CF₃ | H | R12 | Me | H | COMe | Me | H | R22 | Cl | H | CONMe₂ |
| CF₃ | H | R13 | Me | H | COEt | Me | H | R23 | Cl | H | R1 |
| CF₃ | H | R14 | Me | H | COnPr | Me | H | R24 | Cl | H | R2 |
| CF₃ | H | R15 | Me | H | COnBu | Me | H | R25 | Cl | H | R3 |
| CF₃ | H | R16 | Me | H | COPh | Me | H | R26 | Cl | H | R4 |
| CF₃ | H | R17 | Me | H | COCCl₄ | Me | H | R27 | Cl | H | R5 |
| CF₃ | H | R18 | Me | H | COCF₄ | Me | H | R28 | Cl | H | R6 |
| CF₃ | H | R19 | Me | H | CO₂Me | Me | H | R29 | Cl | H | R7 |
| CF₃ | H | R20 | Me | H | CO₂nBu | Me | H | R30 | Cl | H | R8 |
| Cl | H | R9 | Cl | H | SO₂iPr | Br | H | R19 | I | H | COPh |
| Cl | H | R10 | Cl | H | R36 | Br | H | R20 | CN | H | COtBu |
| Cl | H | R11 | Br | H | COtBu | Br | H | R21 | CN | H | COMe |
| Cl | H | R12 | Br | H | COMe | Br | H | R22 | CN | H | COPh |
| Cl | H | R13 | Br | H | COEt | Br | H | R23 | CO₂Me | H | COtBu |
| Cl | H | R14 | Br | H | COnPr | Br | H | R24 | CO₂Me | H | COMe |
| Cl | H | R15 | Br | H | COnBu | Br | H | R25 | CO₂Me | H | COPh |
| Cl | H | R16 | Br | H | COPh | Br | H | R26 | CO₂Et | H | COtBu |
| Cl | H | R17 | Br | H | COCCl₃ | Br | H | R27 | CO₂Et | H | COMe |
| Cl | H | R18 | Br | H | COCF₄ | Br | H | R28 | CO₂Et | H | COPh |
| Cl | H | R19 | Br | H | CO₂Me | Br | H | R29 | Et | H | COtBu |
| Cl | H | R20 | Br | H | CO₂nBu | Br | H | R30 | Et | H | COMe |
| Cl | H | R21 | Br | H | CO₂CH₂Ph | Br | H | R31 | Et | H | COPh |
| Cl | H | R22 | Br | H | CONMe₂ | Br | H | R32 | iPr | H | COtBu |
| Cl | H | R23 | Br | H | R1 | Br | H | R33 | iPr | H | COMe |
| Cl | H | R24 | Br | H | R2 | Br | H | R34 | iPr | H | COPh |
| Cl | H | R25 | Br | H | R3 | Br | H | R35 | CH₂CF₃ | H | COtBu |
| Cl | H | R26 | Br | H | R4 | Br | H | Me | CH₂CF₃ | H | COMe |
| Cl | H | R27 | Br | H | R5 | Br | H | CH₂Ph | CH₂CF₃ | H | COPh |
| Cl | H | R28 | Br | H | R6 | Br | H | SO₂Me | OMe | H | COtBu |
| Cl | H | R29 | Br | H | R7 | Br | H | SO₂Et | OMe | H | COMe |
| Cl | H | R30 | Br | H | R8 | Br | H | SO₂nPr | OMe | H | COPh |
| Cl | H | R31 | Br | H | R9 | Br | H | SO₂iPr | OEt | H | COtBu |
| Cl | H | R32 | Br | H | R10 | Br | H | R36 | OEt | H | COMe |
| Cl | H | R33 | Br | H | R11 | F | H | COtBu | OEt | H | COPh |
| Cl | H | R34 | Br | H | R12 | F | H | COMe | OiPr | H | COtBu |
| Cl | H | R35 | Br | H | R13 | F | H | COPh | OiPr | H | COMe |
| Cl | H | Me | Br | H | R14 | F | H | R1 | OiPr | H | COPh |
| Cl | H | CH₂Ph | Br | H | R15 | F | H | R2 | OCF₃ | H | COtBu |
| Cl | H | SO₂Me | Br | H | R16 | F | H | R25 | OCF₃ | H | COMe |
| Cl | H | SO₂Et | Br | H | R17 | I | H | COtBu | OCF₃ | H | COPh |
| Cl | H | SO₂nPr | Br | H | R18 | I | H | COMe | OPh | H | COtBu |
| OPh | H | COMe | F | F | R19 | F | Me | CO₂Me | F | Me | R29 |
| OPh | H | COPh | F | F | R20 | F | Me | CO₂nBu | F | Me | R30 |
| F | F | COtBu | F | F | R21 | F | Me | CO₂CH₂Ph | F | Me | R31 |
| F | F | COMe | F | F | R22 | F | Me | CONMe₂ | F | Me | R32 |
| F | F | COEt | F | F | R23 | F | Me | R1 | F | Me | R33 |
| F | F | COnPr | F | F | R24 | F | Me | R2 | F | Me | R34 |
| F | F | COnBu | F | F | R25 | F | Me | R3 | F | Me | R35 |
| F | F | COPh | F | F | R26 | F | Me | R4 | F | Me | Me |
| F | F | COCCl₃ | F | F | R27 | F | Me | R5 | F | Me | CH₂Ph |
| F | F | COCF₃ | F | F | R28 | F | Me | R6 | F | Me | SO₂Me |
| F | F | CO₂Me | F | F | R29 | F | Me | R7 | F | Me | SO₂Et |
| F | F | CO₂nBu | F | F | R30 | F | Me | R8 | F | Me | SO₂nPr |
| F | F | CO₂CH₂Ph | F | F | R31 | F | Me | R9 | F | Me | SO₂iPr |
| F | F | CONMe₂ | F | F | R32 | F | Me | R10 | F | Me | R36 |
| F | F | R1 | F | F | R33 | F | Me | R11 | F | Cl | COtBu |
| F | F | R2 | F | F | R34 | F | Me | R12 | F | Cl | COMe |
| F | F | R3 | F | F | R35 | F | Me | R13 | F | Cl | COEt |
| F | F | R4 | F | F | Me | F | Me | R14 | F | Cl | COnPr |
| F | F | R5 | F | F | CH₂Ph | F | Me | R15 | F | Cl | COnBu |
| F | F | R6 | F | F | SO₂Me | F | Me | R16 | F | Cl | COPh |
| F | F | R7 | F | F | SO₂Et | F | Me | R17 | F | Cl | COCCl₃ |
| F | F | R8 | F | F | SO₂nPr | F | Me | R18 | F | Cl | COCF₃ |
| F | F | R9 | F | F | SO₃iPr | F | Me | R19 | F | Cl | CO₂Me |
| F | F | R10 | F | F | R36 | F | Me | R20 | F | Cl | CO₂nBu |
| F | F | R11 | F | Me | COtBu | F | Me | R21 | F | Cl | CO₂CH₂Ph |
| F | F | R12 | F | Me | COMe | F | Me | R22 | F | Cl | CONMe₂ |
| F | F | R13 | F | Me | COEt | F | Me | R23 | F | Cl | R1 |
| F | F | R14 | F | Me | COnPr | F | Me | R24 | F | Cl | R2 |
| F | F | R15 | F | Me | COnBu | F | Me | R25 | F | Cl | R3 |
| F | F | R16 | F | Me | COPh | F | Me | R26 | F | Cl | R4 |
| F | F | R17 | F | Me | COCCl₃ | F | Me | R27 | F | Cl | R5 |
| F | F | R18 | F | Me | COCF₃ | F | Me | R28 | F | Cl | R6 |
| F | Cl | R7 | F | Cl | SO₂Et | CH₂F | H | CO₂CH₂Ph | CH₂F | H | R31 |
| F | Cl | R8 | F | Cl | SOnPr | CH₂F | H | CONMe₂ | CH₂F | H | R32 |

TABLE 1-continued

| | | | | | | | | | | | |
|---|---|---|---|---|---|---|---|---|---|---|---|
| F | Cl | R9 | F | Cl | SO₂iPr | CH₂F | H | R1 | CH₂F | H | R33 |
| F | Cl | R10 | F | Cl | R36 | CH₂F | H | R2 | CH₂F | H | R34 |
| F | Cl | R11 | F | OMe | COtBu | CH₂F | H | R3 | CH₂F | H | R35 |
| F | Cl | R12 | F | OMe | COMe | CH₂F | H | R4 | CH₂F | H | Me |
| F | Cl | R13 | F | OMe | COPh | CH₂F | H | R5 | CH₂F | H | CH₂Ph |
| F | Cl | R14 | F | CF₃ | COtBu | CH₂F | H | R6 | CH₂F | H | SO₂Me |
| F | Cl | R15 | F | CF₃ | COMe | CH₂F | H | R7 | CH₂F | H | SO₂Et |
| F | Cl | R16 | F | CF₃ | COPh | CH₂F | H | R8 | CH₂F | H | SO₂nPr |
| F | Cl | R17 | Cl | Cl | COtBu | CH₂F | H | R9 | CH₂F | H | SO₂iPr |
| F | Cl | R18 | Cl | Cl | COMe | CH₂F | H | R10 | CH₂F | H | R36 |
| F | Cl | R19 | Cl | Cl | COPh | CH₂F | H | R11 | | | |
| F | Cl | R20 | Cl | Me | COtBu | CH₂F | H | R12 | | | |
| F | Cl | R21 | Cl | Me | COMe | CH₂F | H | R13 | | | |
| F | Cl | R22 | Cl | Me | COPh | CH₂F | H | R14 | | | |
| F | Cl | R23 | Me | Me | COtBu | CH₂F | H | R15 | | | |
| F | Cl | R24 | Me | Me | COMe | CH₂F | H | R16 | | | |
| F | Cl | R25 | Me | Me | COPh | CH₂F | H | R17 | | | |
| F | Cl | R26 | OMe | OMe | COtBu | CH₂F | H | R18 | | | |
| F | Cl | R27 | OMe | OMe | COMe | CH₂F | H | R19 | | | |
| F | Cl | R28 | OMe | OMe | COPh | CH₂F | H | R20 | | | |
| F | Cl | R29 | CH₂F | H | COtBu | CH₂F | H | R21 | | | |
| F | Cl | R30 | CH₂F | H | COMe | CH₂F | H | R22 | | | |
| F | Cl | R31 | CH₂F | H | COEt | CH₂F | H | R23 | | | |
| F | Cl | R32 | CH₂F | H | COnPr | CH₂F | H | R24 | | | |
| F | Cl | R33 | CH₂F | H | COnBu | CH₂F | H | R25 | | | |
| F | Cl | R34 | CH₂F | H | COPh | CH₂F | H | R26 | | | |
| F | Cl | R35 | CH₂F | H | COCCl₃ | CH₂F | H | R27 | | | |
| F | Cl | Me | CH₂F | H | COCF₃ | CH₂F | H | R28 | | | |
| F | Cl | CH₂Ph | CH₂F | H | CO₂Me | CH₂F | H | R29 | | | |
| F | Cl | SO₂Me | CH₂F | H | CO₂nBu | CH₂F | H | R30 | | | |

TABLE 2

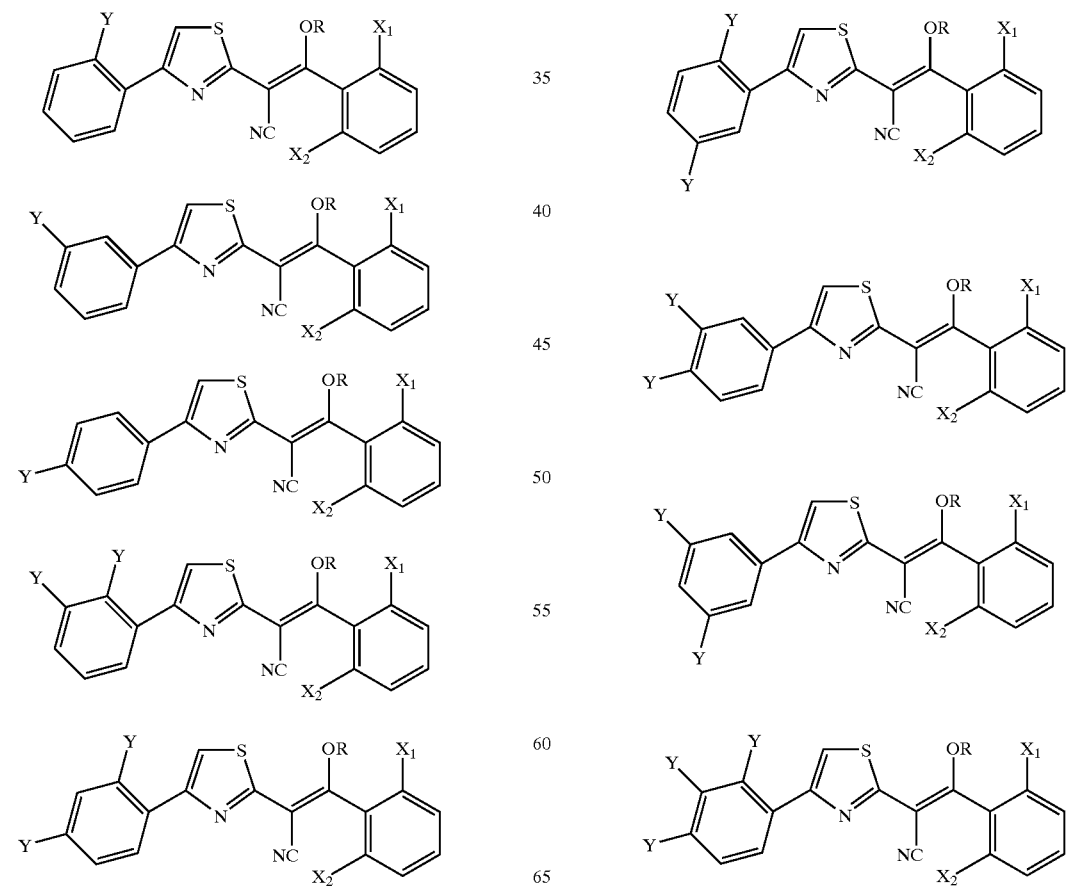

TABLE 2-continued

TABLE 2-continued

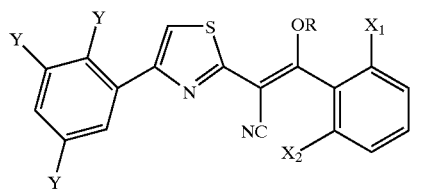
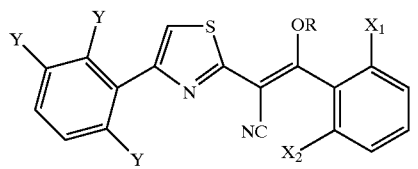
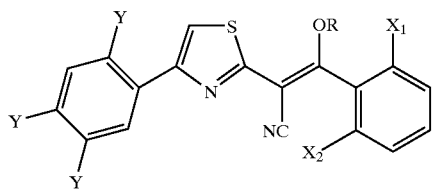
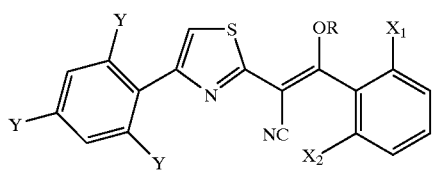
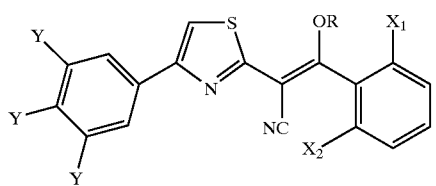
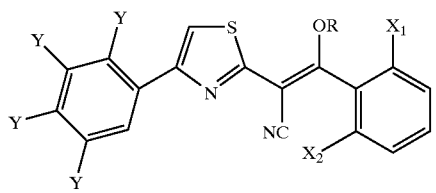
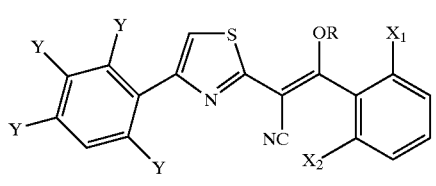
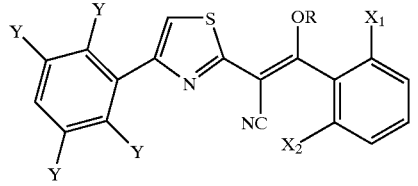

TABLE 2-continued

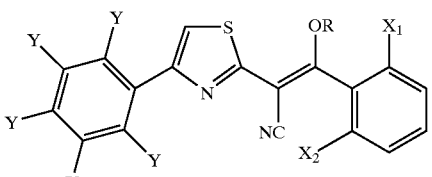

| Y | $X_1$ | $X_2$ | R |
|---|---|---|---|
| F | $CF_3$ | H | COtBu |
| F | $CF_3$ | H | COMe |
| F | $CF_3$ | H | COEt |
| F | $CF_3$ | H | COnPr |
| F | $CF_3$ | H | COnBu |
| F | $CF_3$ | H | COPh |
| F | $CF_3$ | H | $COCCl_3$ |
| F | $CF_3$ | H | $COCF_3$ |
| F | $CF_3$ | H | $CO_2Me$ |
| F | $CF_3$ | H | $CO_2nBu$ |
| F | $CF_3$ | H | $CO_2CH_2Ph$ |
| F | $CF_3$ | H | $CONMe_2$ |
| F | $CF_3$ | H | R1 |
| F | $CF_3$ | H | R2 |
| F | $CF_3$ | H | R3 |
| F | $CF_3$ | H | R4 |
| F | $CF_3$ | H | R5 |
| F | $CF_3$ | H | R6 |
| F | $CF_3$ | H | R7 |
| F | $CF_3$ | H | R8 |
| F | $CF_3$ | H | R9 |
| F | $CF_3$ | H | R10 |
| F | $CF_3$ | H | R11 |
| F | $CF_3$ | H | R12 |
| F | $CF_3$ | H | R13 |
| F | $CF_3$ | H | R14 |
| F | $CF_3$ | H | R15 |
| F | $CF_3$ | H | R16 |
| F | $CF_3$ | H | R17 |
| F | $CF_3$ | H | R18 |
| F | $CF_3$ | H | R19 |
| F | $CF_3$ | H | R20 |
| F | $CF_3$ | H | R21 |
| F | $CF_3$ | H | R22 |
| F | $CF_3$ | H | R23 |
| F | $CF_3$ | H | R24 |
| F | $CF_3$ | H | R25 |
| F | $CF_3$ | H | R26 |
| F | $CF_3$ | H | R27 |
| F | $CF_3$ | H | R28 |
| F | $CF_3$ | H | R29 |
| F | $CF_3$ | H | R30 |
| F | $CF_3$ | H | R31 |
| F | $CF_3$ | H | R32 |
| F | $CF_3$ | H | R33 |
| F | $CF_3$ | H | R34 |
| F | $CF_3$ | H | R35 |
| F | $CF_3$ | H | Me |
| F | $CF_3$ | H | $CH_2Ph$ |
| F | $CF_3$ | H | $SO_2Me$ |
| F | $CF_3$ | H | $SO_2Et$ |
| F | $CF_3$ | H | $SO_2nPr$ |
| F | $CF_3$ | H | $SO_2iPr$ |
| F | $CF_3$ | H | R36 |
| F | Me | H | COtBu |
| F | Me | H | COMe |
| F | Me | H | COEt |
| F | Me | H | COnPr |
| F | Me | H | COnBu |
| F | Me | H | COPh |
| F | Me | H | $COCCl_3$ |
| F | Me | H | $COCF_3$ |
| F | Me | H | $CO_2Me$ |
| F | Me | H | $CO_2nBu$ |
| F | Me | H | $CO_2CH_2Ph$ |
| F | Me | H | $CONMe_2$ |
| F | Me | H | R1 |

TABLE 2-continued

| | | | |
|---|---|---|---|
| F | Me | H | R2 |
| F | Me | H | R3 |
| F | Me | H | R4 |
| F | Me | H | R5 |
| F | Me | H | R6 |
| F | Me | H | R7 |
| F | Me | H | R8 |
| F | Me | H | R9 |
| F | Me | H | R10 |
| F | Me | H | R11 |
| F | Me | H | R12 |
| F | Me | H | R13 |
| F | Me | H | R14 |
| F | Me | H | R15 |
| F | Me | H | R16 |
| F | Me | H | R17 |
| F | Me | K | R18 |
| F | Me | H | R19 |
| F | Me | H | R20 |
| F | Me | H | R21 |
| F | Me | H | R22 |
| F | Me | H | R23 |
| F | Me | H | R24 |
| F | Me | H | R25 |
| F | Me | H | R26 |
| F | Me | H | R27 |
| F | Me | H | R28 |
| F | Me | H | R29 |
| F | Me | H | R30 |
| F | Me | H | R31 |
| F | Me | H | R32 |
| F | Me | H | R33 |
| F | Me | H | R34 |
| F | Me | H | R35 |
| F | Me | H | Me |
| F | Me | H | $CH_2Ph$ |
| F | Me | H | $SO_2Me$ |
| F | Me | H | $SO_2Et$ |
| F | Me | H | $SO_2nPr$ |
| F | Me | H | $SO_2iPr$ |
| F | Me | H | R36 |
| F | Cl | H | COtBu |
| F | Cl | H | COMe |
| F | Cl | H | COEt |
| F | Cl | H | COnPr |
| F | Cl | H | COnBu |
| F | Cl | H | COPh |
| F | Cl | H | $COCCl_3$ |
| F | Cl | H | $COCF_3$ |
| F | Cl | H | $CO_2Me$ |
| F | Cl | H | $CO_2nBu$ |
| F | Cl | H | $CO_2CH_2Ph$ |
| F | Cl | H | $CONMe_2$ |
| F | Cl | H | R1 |
| F | Cl | H | R2 |
| F | Cl | H | R3 |
| F | Cl | H | R4 |
| F | Cl | H | R5 |
| F | Cl | H | R6 |
| F | Cl | H | R7 |
| F | Cl | H | R8 |
| F | Cl | H | R9 |
| F | Cl | H | R10 |
| F | Cl | H | R11 |
| F | Cl | H | R12 |
| F | Cl | H | R13 |
| F | Cl | H | R14 |
| F | Cl | H | R15 |
| F | Cl | H | R16 |
| F | Cl | H | R17 |
| F | Cl | H | R18 |
| F | Cl | H | R19 |
| F | Cl | H | R20 |
| F | Cl | H | R21 |
| F | Cl | H | R22 |
| F | Cl | H | R23 |
| F | Cl | H | R24 |
| F | Cl | H | R25 |
| F | Cl | H | R26 |
| F | Cl | H | R27 |
| F | Cl | H | R28 |
| F | Cl | H | R29 |
| F | Cl | H | R30 |
| F | Cl | H | R31 |
| F | Cl | H | R32 |
| F | Cl | H | R33 |
| F | Cl | H | R34 |
| F | Cl | H | R35 |
| F | Cl | H | Me |
| F | Cl | H | $CH_2Ph$ |
| F | Cl | H | $SO_2Me$ |
| F | Cl | H | $SO_2Et$ |
| F | Cl | H | $SO_2nPr$ |
| F | Cl | H | $SO_2iPr$ |
| F | Cl | H | R36 |
| F | Br | H | COtBu |
| F | Br | H | COMe |
| F | Br | H | COEt |
| F | Br | H | COnPr |
| F | Br | H | COnBu |
| F | Br | H | COPh |
| F | Br | H | $COCCl_3$ |
| F | Br | H | $COCF_3$ |
| F | Br | H | $CO_2Me$ |
| F | Br | H | $CO_2nBu$ |
| F | Br | H | $CO_2CH_2Ph$ |
| F | Br | H | $CONMe_2$ |
| F | Br | H | R1 |
| F | Br | H | R2 |
| F | Br | H | R3 |
| F | Br | H | R4 |
| F | Br | H | R5 |
| F | Br | H | R6 |
| F | Br | H | R7 |
| F | Br | H | R8 |
| F | Br | H | R9 |
| F | Br | H | R10 |
| F | Br | H | R11 |
| F | Br | H | R12 |
| F | Br | H | R13 |
| F | Br | H | R14 |
| F | Br | H | R15 |
| F | Br | H | R16 |
| F | Br | H | R17 |
| F | Br | H | R18 |
| F | Br | H | R19 |
| F | Br | H | R20 |
| F | Br | H | R21 |
| F | Br | H | R22 |
| F | Br | H | R23 |
| F | Br | H | R24 |
| F | Br | H | R25 |
| F | Br | H | R26 |
| F | Br | H | R27 |
| F | Br | H | R28 |
| F | Br | H | R29 |
| P | Br | H | R30 |
| F | Br | H | R31 |
| F | Br | H | R32 |
| P | Br | H | R33 |
| F | Br | H | R34 |
| F | Br | H | R35 |
| F | Br | H | Me |
| F | Br | H | $CH_2Ph$ |
| F | Br | H | $SO_2Me$ |
| F | Br | H | $SO_2Et$ |
| F | Br | H | $SO_2nPr$ |
| F | Br | H | $SO_2iPr$ |
| F | Br | H | R36 |
| F | F | H | COtBu |
| F | F | H | COMe |
| F | F | H | COPh |
| F | F | H | R1 |
| F | F | H | R2 |
| F | F | H | R25 |
| F | I | H | COtBu |
| F | I | H | COMe |
| F | I | H | COPh |

TABLE 2-continued

| | | | |
|---|---|---|---|
| F | CN | H | COtBu |
| F | CN | H | COMe |
| F | CN | H | COPh |
| F | CO2Me | H | COtBu |
| F | CO2Me | H | COMe |
| F | CO2Me | H | COPh |
| F | CO2Et | H | COtBu |
| F | CO2Et | H | COMe |
| F | CO2Et | H | COPh |
| F | Et | H | COtBu |
| F | Et | H | COMe |
| F | Et | H | COPh |
| F | iPr | H | COtBu |
| F | iPr | H | COMe |
| F | iPr | H | COPh |
| F | CH2CF3 | H | COtBu |
| F | CH2CF3 | H | COMe |
| F | CH2CF3 | H | COPh |
| F | OMe | H | COtBu |
| F | OMe | H | COMe |
| F | OMe | H | COPh |
| F | OEt | H | COtBu |
| F | OEt | H | COMe |
| F | OEt | H | COPh |
| F | OiPr | H | COtBu |
| F | OiPr | H | COMe |
| F | OiPr | H | COPh |
| F | OCF3 | H | COtBu |
| F | OCF3 | H | COMe |
| F | OCF3 | H | COPh |
| F | OPh | H | COtBu |
| F | OPh | H | COMe |
| F | OPh | H | COPh |
| F | F | F | COtBu |
| F | F | F | COMe |
| F | F | F | COEt |
| F | F | F | COnPr |
| F | F | F | COnBu |
| F | F | F | COPh |
| F | F | F | COCCl3 |
| F | F | F | COCF3 |
| F | F | F | CO2Me |
| F | F | F | CO2Bu |
| F | F | F | CO2CH2Ph |
| F | F | F | CONMe2 |
| F | F | F | R1 |
| F | F | F | R2 |
| F | F | F | R3 |
| F | F | F | R4 |
| F | F | F | R5 |
| F | F | F | R6 |
| F | F | F | R7 |
| F | F | F | R8 |
| F | F | F | R9 |
| F | F | F | R10 |
| F | F | F | R11 |
| F | F | F | R12 |
| F | F | F | R13 |
| F | F | F | R14 |
| F | F | F | R15 |
| F | F | F | R16 |
| F | F | F | R17 |
| F | F | F | R18 |
| F | F | F | R19 |
| F | F | F | R20 |
| F | F | F | R21 |
| F | F | F | R22 |
| F | F | F | R23 |
| F | F | F | R24 |
| F | F | F | R25 |
| F | F | F | R26 |
| F | F | F | R27 |
| F | F | F | R28 |
| F | F | F | R29 |
| F | F | F | R30 |
| F | F | F | R31 |
| F | F | F | R32 |
| F | F | F | R33 |
| F | F | F | R34 |
| F | F | F | R35 |
| F | F | F | Me |
| F | F | F | CH2Ph |
| F | F | F | SO2Me |
| F | F | F | SO2Et |
| F | F | F | SO2nPr |
| F | F | F | SO2iPr |
| F | F | F | R36 |
| F | F | Me | COtBu |
| F | F | Me | COMe |
| F | F | Me | COEt |
| F | F | Me | COnPr |
| F | F | Me | COnBu |
| F | F | Me | COPh |
| F | F | Me | COCCl3 |
| F | F | Me | COCF3 |
| F | F | Me | CO2Me |
| F | F | Me | CO2nBu |
| F | F | Me | CO2CH2Ph |
| F | F | Me | CONMe2 |
| F | F | Me | R1 |
| F | F | Me | R2 |
| F | F | Me | R3 |
| F | F | Me | R4 |
| F | F | Me | R5 |
| F | F | Me | R6 |
| F | F | Me | R7 |
| F | F | Me | R8 |
| F | F | Me | R9 |
| F | F | Me | R10 |
| F | F | Me | R11 |
| F | F | Me | R12 |
| F | F | Me | R13 |
| F | F | Me | R14 |
| F | F | Me | R15 |
| F | F | Me | R16 |
| F | F | Me | R17 |
| F | F | Me | R18 |
| F | F | Me | R19 |
| F | F | Me | R20 |
| F | F | Me | R21 |
| F | F | Me | R22 |
| F | F | Me | R23 |
| F | F | Me | R24 |
| F | F | Me | R25 |
| F | F | Me | R26 |
| F | F | Me | R27 |
| F | F | Me | R28 |
| F | F | Me | R29 |
| F | F | Me | R30 |
| F | F | Me | R31 |
| F | F | Me | R32 |
| F | F | Me | R33 |
| F | F | Me | R34 |
| F | F | Me | R35 |
| F | F | Me | Me |
| F | F | Me | CH2Ph |
| F | F | Me | SO2Me |
| F | F | Me | SO2Et |
| F | F | Me | SO2nPr |
| F | F | Me | SO2iPr |
| F | F | Me | R36 |
| F | F | Cl | COtBu |
| F | F | Cl | COMe |
| F | F | Cl | COEt |
| F | F | Cl | COnPr |
| F | F | Cl | COnBu |
| F | F | Cl | COPh |
| F | F | Cl | COCCl3 |
| F | F | Cl | COCF3 |
| F | F | Cl | CO2Me |
| F | F | Cl | CO2nBu |
| F | F | Cl | CO2CH2Ph |
| F | F | Cl | CONMe2 |
| F | F | Cl | R1 |
| F | F | Cl | R2 |
| F | F | Cl | R3 |
| F | F | Cl | R4 |
| F | F | Cl | R5 |

TABLE 2-continued

| | | | |
|---|---|---|---|
| F | F | Cl | R6 |
| F | F | Cl | R7 |
| F | F | Cl | R8 |
| F | F | Cl | R9 |
| F | F | Cl | R10 |
| F | F | Cl | R11 |
| F | F | Cl | R12 |
| F | F | Cl | R13 |
| F | F | Cl | R14 |
| F | F | Cl | R15 |
| F | F | Cl | R16 |
| F | F | Cl | R17 |
| F | F | Cl | R18 |
| F | F | Cl | R19 |
| F | F | Cl | R20 |
| F | F | Cl | R21 |
| F | F | Cl | R22 |
| F | F | Cl | R23 |
| F | F | Cl | R24 |
| F | F | Cl | R25 |
| F | F | Cl | R26 |
| F | F | Cl | R27 |
| F | F | Cl | R28 |
| F | F | Cl | R29 |
| F | F | Cl | R30 |
| F | F | Cl | R31 |
| F | F | Cl | R32 |
| F | F | Cl | R33 |
| F | F | Cl | R34 |
| F | F | Cl | R35 |
| F | F | Cl | Me |
| F | F | Cl | $CH_2Ph$ |
| F | F | Cl | $SO_2Me$ |
| F | F | Cl | $SO_2Et$ |
| F | F | Cl | $SO_2nPr$ |
| F | F | Cl | $SO_2iPr$ |
| F | F | Cl | R36 |
| F | F | OMe | COtBu |
| F | F | OMe | COMe |
| F | F | OMe | COPh |
| F | F | $CF_3$ | COtBu |
| F | F | $CF_3$ | COMe |
| F | F | $CF_3$ | COPh |
| F | Cl | Cl | COtBu |
| F | Cl | Cl | COMe |
| F | Cl | Cl | COPh |
| F | Cl | Me | COtBu |
| F | Cl | Me | COMe |
| F | Cl | Me | COPh |
| F | Me | Me | COtBu |
| F | Me | Me | COMe |
| F | Me | Me | COPh |
| F | OMe | OMe | COtBu |
| F | OMe | OMe | COMe |
| F | OMe | OMe | COPh |
| Me | $CF_3$ | H | COtBu |
| Me | $CF_3$ | H | COMe |
| Me | $CF_3$ | H | COEt |
| Me | $CF_3$ | H | COnPr |
| Me | $CF_3$ | H | COnBu |
| Me | $CF_3$ | H | COPh |
| Me | $CF_3$ | H | $COCCl_3$ |
| Me | $CF_3$ | H | $COCF_3$ |
| Me | $CF_3$ | H | $CO_2Me$ |
| Me | $CF_3$ | H | $CO_2nBu$ |
| Me | $CF_3$ | H | $CO_2CH_2Ph$ |
| Me | $CF_3$ | H | $CONMe_2$ |
| Me | $CF_3$ | H | R1 |
| Me | $CF_3$ | H | R2 |
| Me | $CF_3$ | H | R3 |
| Me | $CF_3$ | H | R4 |
| Me | $CF_3$ | H | R5 |
| Me | $CF_3$ | H | R6 |
| Me | $CF_3$ | H | R7 |
| Me | $CF_3$ | H | R8 |
| Me | $CF_3$ | H | R9 |
| Me | $CF_3$ | H | R10 |
| Me | $CF_3$ | H | R11 |
| Me | $CF_3$ | H | R12 |
| Me | $CF_3$ | H | R13 |
| Me | $CF_3$ | H | R14 |
| Me | $CF_3$ | H | R15 |
| Me | $CF_3$ | H | R16 |
| Me | $CF_3$ | H | R17 |
| Me | $CF_3$ | H | R18 |
| Me | $CF_3$ | H | R19 |
| Me | $CF_3$ | H | R20 |
| Me | $CF_3$ | H | R21 |
| Me | $CF_3$ | H | R22 |
| Me | $CF_3$ | H | R23 |
| Me | $CF_3$ | H | R24 |
| Me | $CF_3$ | H | R25 |
| Me | $CF_3$ | H | R26 |
| Me | $CF_3$ | H | R27 |
| Me | $CF_3$ | H | R28 |
| Me | $CF_3$ | H | R29 |
| Me | $CF_3$ | H | R30 |
| Me | $CF_3$ | H | R31 |
| Me | $CF_3$ | H | R32 |
| Me | $CF_3$ | H | R33 |
| Me | $CF_3$ | H | R34 |
| Me | $CF_3$ | H | R35 |
| Me | $CF_3$ | H | Me |
| Me | $CF_3$ | H | $CH_2Ph$ |
| Me | $CF_3$ | H | $SO_2Me$ |
| Me | $CF_3$ | H | $SO_2Et$ |
| Me | $CF_3$ | H | $SO_2nPr$ |
| Me | $CF_3$ | H | $SO_2iPr$ |
| Me | $CF_3$ | H | R36 |
| Me | Me | H | COtBu |
| Me | Me | H | COMe |
| Me | Me | H | COEt |
| Me | Me | H | COnPr |
| Me | Me | H | COnBu |
| Me | Me | H | COPh |
| Me | Me | H | $COCCl_3$ |
| Me | Me | H | $COCF_3$ |
| Me | Me | H | $CO_2Me$ |
| Me | Me | H | $CO_2tBu$ |
| Me | Me | H | $CO_2CH_2Ph$ |
| Me | Me | H | $CONMe_2$ |
| Me | Me | H | R1 |
| Me | Me | H | R2 |
| Me | Me | H | R3 |
| Me | Me | H | R4 |
| Me | Me | H | R5 |
| Me | Me | H | R6 |
| Me | Me | H | R7 |
| Me | Me | H | R8 |
| Me | Me | H | R9 |
| Me | Me | H | R10 |
| Me | Me | H | R11 |
| Me | Me | H | R12 |
| Me | Me | H | R13 |
| Me | Me | H | R14 |
| Me | Me | H | R15 |
| Me | Me | H | R16 |
| Me | Me | H | R17 |
| Me | Me | H | R18 |
| Me | Me | H | R19 |
| Me | Me | H | R20 |
| Me | Me | H | R21 |
| Me | Me | H | R22 |
| Me | Me | H | R23 |
| Me | Me | H | R24 |
| Me | Me | H | R25 |
| Me | Me | H | R26 |
| Me | Me | H | R27 |
| Me | Me | H | R28 |
| Me | Me | H | R29 |
| Me | Me | H | R30 |
| Me | Me | H | R31 |
| Me | Me | H | R32 |
| Me | Me | H | R33 |
| Me | Me | H | R34 |
| Me | Me | H | R35 |
| Me | Me | H | Me |
| Me | Me | H | $CH_2Ph$ |

TABLE 2-continued

| | | | |
|---|---|---|---|
| Me | Me | H | SO$_2$Me |
| Me | Me | H | SO$_2$Et |
| Me | Me | H | SO$_2$nPr |
| Me | Me | H | SO$_2$iPr |
| Me | Me | H | R36 |
| Me | Cl | H | COtBu |
| Me | Cl | H | COMe |
| Me | Cl | H | COEt |
| Me | Cl | H | COnPr |
| Me | Cl | H | COnBu |
| Me | Cl | H | COPh |
| Me | Cl | H | COCCl$_3$ |
| Me | Cl | H | COCF$_3$ |
| Me | Cl | H | CO$_2$Me |
| Me | Cl | H | CO$_2$nBu |
| Me | Cl | H | CO$_2$CH$_2$Ph |
| Me | Cl | H | CONMe$_2$ |
| Me | Cl | H | R1 |
| Me | Cl | H | R2 |
| Me | Cl | H | R3 |
| Me | Cl | H | R4 |
| Me | Cl | H | R5 |
| Me | Cl | H | R6 |
| Me | Cl | H | R7 |
| Me | Cl | H | R8 |
| Me | Cl | H | R9 |
| Me | Cl | H | R10 |
| Me | Cl | H | R11 |
| Me | Cl | H | R12 |
| Me | Cl | H | R13 |
| Me | Cl | H | R14 |
| Me | Cl | H | R15 |
| Me | Cl | H | R16 |
| Me | Cl | H | R17 |
| Me | Cl | H | R18 |
| Me | Cl | H | R19 |
| Me | Cl | H | R20 |
| Me | Cl | H | R21 |
| Me | Cl | H | R22 |
| Me | Cl | H | R23 |
| Me | Cl | H | R24 |
| Me | Cl | H | R25 |
| Me | Cl | H | R26 |
| Me | Cl | H | R27 |
| Me | Cl | H | R28 |
| Me | Cl | H | R29 |
| Me | Cl | H | R30 |
| Me | Cl | H | R31 |
| Me | Cl | H | R32 |
| Me | Cl | H | R33 |
| Me | Cl | H | R34 |
| Me | Cl | H | R35 |
| Me | Cl | H | Me |
| Me | Cl | H | CH$_2$Ph |
| Me | Cl | H | SO$_2$Me |
| Me | Cl | H | SO$_2$Et |
| Me | Cl | H | SO$_2$nPr |
| Me | Cl | H | SO$_2$iPr |
| Me | Cl | H | R36 |
| Me | Br | H | COtBu |
| Me | Br | H | COMe |
| Me | Br | H | COtBu |
| Me | F | H | COtBu |
| Me | F | H | COMe |
| Me | F | H | COtBu |
| Me | I | H | COtBu |
| Me | I | H | COMe |
| Me | I | H | COPh |
| Me | CN | H | COtBu |
| Me | CN | H | COMe |
| Me | CN | H | COPh |
| Me | CO$_2$Me | H | COtBu |
| Me | CO$_2$Me | H | COMe |
| Me | CO$_2$Me | H | COPh |
| Me | CO$_2$Et | H | COtBu |
| Me | CO$_2$Et | H | COMe |
| Me | CO$_2$Et | H | COPh |
| Me | Et | H | COtBu |
| Me | Et | H | COMe |
| Me | Et | H | COPh |
| Me | iPr | H | COtBu |
| Me | iPr | H | COMe |
| Me | iPr | H | COPh |
| Me | CH$_2$CF$_3$ | H | COtBu |
| Me | CH$_2$CF$_3$ | H | COMe |
| Me | CH$_2$CF$_3$ | H | COPh |
| Me | OMe | H | COtBu |
| Me | OMe | H | COMe |
| Me | OMe | H | COPh |
| Me | OEt | H | COtBu |
| Me | OEt | H | COMe |
| Me | OEt | H | COPh |
| Me | OiPr | H | COtBu |
| Me | OiPr | H | COMe |
| Me | OiPr | H | COPh |
| Me | OCF$_3$ | H | COtBu |
| Me | OCF$_3$ | H | COMe |
| Me | OCF$_3$ | H | COPh |
| Me | OPh | H | COtBu |
| Me | OPh | H | COMe |
| Me | OPh | H | COPh |
| Me | F | F | COtBu |
| Me | F | F | COMe |
| Me | F | F | COEt |
| Me | F | F | COnPr |
| Me | F | F | COnBu |
| Me | F | F | COPh |
| Me | F | F | COCCl$_3$ |
| Me | F | F | COCF$_3$ |
| Me | F | F | CO$_2$Me |
| Me | F | F | CO$_2$nBu |
| Me | F | F | CO$_2$CH$_2$Ph |
| Me | F | F | CONMe$_2$ |
| Me | F | F | R1 |
| Me | F | F | R2 |
| Me | F | F | R3 |
| Me | F | F | R4 |
| Me | F | F | R5 |
| Me | F | F | R6 |
| Me | F | F | R7 |
| Me | F | F | R8 |
| Me | F | F | R9 |
| Me | F | F | R10 |
| Me | F | F | R11 |
| Me | F | F | R12 |
| Me | F | F | R13 |
| Me | F | F | R14 |
| Me | F | F | R15 |
| Me | F | F | R16 |
| Me | F | F | R17 |
| Me | F | F | R18 |
| Me | F | F | R19 |
| Me | F | F | R20 |
| Me | F | F | R21 |
| Me | F | F | R22 |
| Me | F | F | R23 |
| Me | F | F | R24 |
| Me | F | F | R25 |
| Me | F | F | R26 |
| Me | F | F | R27 |
| Me | F | F | R28 |
| Me | F | F | R29 |
| Me | F | F | R30 |
| Me | F | F | R31 |
| Me | F | F | R32 |
| Me | F | F | R33 |
| Me | F | F | R34 |
| Me | F | F | R35 |
| Me | F | F | Me |
| Me | F | F | CH$_2$Ph |
| Me | F | F | SO$_2$Me |
| Me | F | F | SO$_2$Et |
| Me | F | F | SO$_2$nPr |
| Me | F | F | SO$_2$iPr |
| Me | F | F | R36 |
| Me | F | Me | COtBu |
| Me | F | Me | COMe |
| Me | F | Me | COEt |

TABLE 2-continued

| | | | |
|---|---|---|---|
| Me | F | Me | COnPr |
| Me | F | Me | COnBu |
| Me | F | Me | COPh |
| Me | F | Me | COCCl$_3$ |
| Me | F | Me | COCF$_3$ |
| Me | F | Me | CO$_2$Me |
| Me | F | Me | CO$_2$nBu |
| Me | F | Me | CO$_2$CH$_2$Ph |
| Me | F | Me | CONMe$_2$ |
| Me | F | Me | R1 |
| Me | F | Me | R2 |
| Me | F | Me | R3 |
| Me | F | Me | R4 |
| Me | F | Me | R5 |
| Me | F | Me | R6 |
| Me | F | Me | R7 |
| Me | F | Me | R8 |
| Me | F | Me | R9 |
| Me | F | Me | R10 |
| Me | F | Me | R11 |
| Me | F | Me | R12 |
| Me | F | Me | R13 |
| Me | F | Me | R14 |
| Me | F | Me | R15 |
| Me | F | Me | R16 |
| Me | F | Me | R17 |
| Me | F | Me | R18 |
| Me | F | Me | R19 |
| Me | F | Me | R20 |
| Me | F | Me | R21 |
| Me | F | Me | R22 |
| Me | F | Me | R23 |
| Me | F | Me | R24 |
| Me | F | Me | R25 |
| Me | F | Me | R26 |
| Me | F | Me | R27 |
| Me | F | Me | R28 |
| Me | F | Me | R29 |
| Me | F | Me | R30 |
| Me | F | Me | R31 |
| Me | F | Me | R32 |
| Me | F | Me | R33 |
| Me | F | Me | R34 |
| Me | F | Me | R35 |
| Me | F | Me | Me |
| Me | F | Me | CH$_2$Ph |
| Me | F | Me | SO$_2$Me |
| Me | F | Me | SO$_2$Et |
| Me | F | Me | SO$_2$nPr |
| Me | F | Me | SO$_2$iPr |
| Me | F | Me | R36 |
| Me | F | Cl | COtBu |
| Me | F | Cl | COMe |
| Me | F | Cl | COEt |
| Me | F | Cl | COnPr |
| Me | F | Cl | COnBu |
| Me | F | Cl | COPh |
| Me | F | Cl | COCCl$_3$ |
| Me | F | Cl | COCF$_3$ |
| Me | F | Cl | CO$_2$Me |
| Me | F | Cl | CO$_2$nBu |
| Me | F | Cl | CO$_2$CH$_2$Ph |
| Me | F | Cl | CONMe$_2$ |
| Me | F | Cl | R1 |
| Me | F | Cl | R2 |
| Me | F | Cl | R3 |
| Me | F | Cl | R4 |
| Me | F | Cl | R5 |
| Me | F | Cl | R6 |
| Me | F | Cl | R7 |
| Me | F | Cl | R8 |
| Me | F | Cl | R9 |
| Me | F | Cl | R10 |
| Me | F | Cl | R11 |
| Me | F | Cl | R12 |
| Me | F | Cl | R13 |
| Me | F | Cl | R14 |
| Me | F | Cl | R15 |
| Me | F | Cl | R16 |
| Me | F | Cl | R17 |
| Me | F | Cl | R18 |
| Me | F | Cl | R19 |
| Me | F | Cl | R20 |
| Me | F | Cl | R21 |
| Me | F | Cl | R22 |
| Me | F | Cl | R23 |
| Me | F | Cl | R24 |
| Me | F | Cl | R25 |
| Me | F | Cl | R26 |
| Me | F | Cl | R27 |
| Me | F | Cl | R28 |
| Me | F | Cl | R29 |
| Me | F | Cl | R30 |
| Me | F | Cl | R31 |
| Me | F | Cl | R32 |
| Me | F | Cl | R33 |
| Me | F | Cl | R34 |
| Me | F | Cl | R35 |
| Me | F | Cl | Me |
| Me | F | Cl | CH$_2$Ph |
| Me | F | Cl | SO$_2$Me |
| Me | F | Cl | SO$_2$Et |
| Me | F | Cl | SO$_2$nPr |
| Me | F | Cl | SO$_2$iPr |
| Me | F | Cl | R36 |
| Me | F | OMe | COtBu |
| Me | F | OMe | COMe |
| Me | F | OMe | COPh |
| Me | F | CF$_3$ | COtBu |
| Me | F | CF$_3$ | COMe |
| Me | F | CF$_3$ | COPh |
| Me | Cl | Cl | COtBu |
| Me | Cl | Cl | COMe |
| Me | Cl | Cl | COPh |
| Me | Cl | Me | COtBu |
| Me | Cl | Me | COMe |
| Me | Cl | Me | COPh |
| Me | Me | Me | COtBu |
| Me | Me | Me | COMe |
| Me | Me | Me | COPh |
| Me | OMe | OMe | COtBu |
| Me | OMe | OMe | COMe |
| Me | OMe | OMe | COPh |
| Cl | CF$_3$ | H | COtBu |
| Cl | CF$_3$ | H | COMe |
| Cl | CF$_3$ | H | COEt |
| Cl | CF$_3$ | H | COnPr |
| Cl | CF$_3$ | H | COnBu |
| Cl | CF$_3$ | H | COPh |
| Cl | CF$_3$ | H | COCCl$_3$ |
| Cl | CF$_3$ | H | COCF$_3$ |
| Cl | CF$_3$ | H | CO$_2$Me |
| Cl | CF$_3$ | H | CO$_2$nBu |
| Cl | CF$_3$ | H | CO$_2$CH$_2$Ph |
| Cl | CF$_3$ | H | CONMe$_2$ |
| Cl | CF$_3$ | H | R1 |
| Cl | CF$_3$ | H | R2 |
| Cl | CF$_3$ | H | R3 |
| Cl | CF$_3$ | H | R4 |
| Cl | CF$_3$ | H | R5 |
| Cl | CF$_3$ | H | R6 |
| Cl | CF$_3$ | H | R7 |
| Cl | CF$_3$ | H | R8 |
| Cl | CF$_3$ | H | R9 |
| Cl | CF$_3$ | H | R10 |
| Cl | CF$_3$ | H | R11 |
| Cl | CF$_3$ | H | R12 |
| Cl | CF$_3$ | H | R13 |
| Cl | CF$_3$ | H | R14 |
| Cl | CF$_3$ | H | R15 |
| Cl | CF$_3$ | H | R16 |
| Cl | CF$_3$ | H | R17 |
| Cl | CF$_3$ | H | R18 |
| Cl | CF$_3$ | H | R19 |
| Cl | CF$_3$ | H | R20 |
| Cl | CF$_3$ | H | R21 |
| Cl | CF$_3$ | H | R22 |
| Cl | CF$_3$ | H | R23 |

TABLE 2-continued

| | | | |
|---|---|---|---|
| Cl | $CF_3$ | H | R24 |
| Cl | $CF_3$ | H | R25 |
| Cl | $CF_3$ | H | R26 |
| Cl | $CF_3$ | H | R27 |
| Cl | $CF_3$ | H | R28 |
| Cl | $CF_3$ | H | R29 |
| Cl | $CF_3$ | H | R30 |
| Cl | $CF_3$ | H | R31 |
| Cl | $CF_3$ | H | R32 |
| Cl | $CF_3$ | H | R33 |
| Cl | $CF_3$ | H | R34 |
| Cl | $CF_3$ | H | R35 |
| Cl | $CF_3$ | H | Me |
| Cl | $CF_3$ | H | $CH_2Ph$ |
| Cl | $CF_3$ | H | $SO_2Me$ |
| Cl | $CF_3$ | H | $SO_2Et$ |
| Cl | $CF_3$ | H | $SO_2nPr$ |
| Cl | $CF_3$ | H | $SO_2iPr$ |
| Cl | $CF_3$ | H | R36 |
| Cl | Me | H | COtBu |
| Cl | Me | H | COMe |
| Cl | Me | H | COEt |
| Cl | Me | H | COnPr |
| Cl | Me | H | COnBu |
| Cl | Me | H | COPh |
| Cl | Me | H | $COCCl_3$ |
| Cl | Me | H | $COCF_3$ |
| Cl | Me | H | $CO_2Me$ |
| Cl | Me | H | $CO_2nBu$ |
| Cl | Me | H | $CO_2CH_2Ph$ |
| Cl | Me | H | $CONMe_2$ |
| Cl | Me | H | R1 |
| Cl | Me | H | R2 |
| Cl | Me | H | R3 |
| Cl | Me | H | R4 |
| Cl | Me | H | R5 |
| Cl | Me | H | R6 |
| Cl | Me | H | R7 |
| Cl | Me | H | R8 |
| Cl | Me | H | R9 |
| Cl | Me | H | R10 |
| Cl | Me | H | R11 |
| Cl | Me | H | R12 |
| Cl | Me | H | R13 |
| Cl | Me | H | R14 |
| Cl | Me | H | R15 |
| Cl | Me | H | R16 |
| Cl | Me | H | R17 |
| Cl | Me | H | R18 |
| Cl | Me | H | R19 |
| Cl | Me | H | R20 |
| Cl | Me | H | R21 |
| Cl | Me | H | R22 |
| Cl | Me | H | R23 |
| Cl | Me | H | R24 |
| Cl | Me | H | R25 |
| Cl | Me | H | R26 |
| Cl | Me | H | R27 |
| Cl | Me | H | R28 |
| Cl | Me | H | R29 |
| Cl | Me | H | R30 |
| Cl | Me | H | R31 |
| Cl | Me | H | R32 |
| Cl | Me | H | R33 |
| Cl | Me | H | R34 |
| Cl | Me | H | R35 |
| Cl | Me | H | Me |
| Cl | Me | H | $CH_2Ph$ |
| Cl | Me | H | $SO_2Me$ |
| Cl | Me | H | $SO_2Et$ |
| Cl | Me | H | $SO_2nPr$ |
| Cl | Me | H | $SO_2iPr$ |
| Cl | Me | H | R36 |
| Cl | Cl | H | COtBu |
| Cl | Cl | H | COMe |
| Cl | Cl | H | COEt |
| Cl | Cl | H | COnPr |
| Cl | Cl | H | COnBu |
| Cl | Cl | H | COPh |
| Cl | Cl | H | $COCCl_3$ |
| Cl | Cl | H | $COCF_3$ |
| Cl | Cl | H | $CO_2Me$ |
| Cl | Cl | H | $CO_2nBu$ |
| Cl | Cl | H | $CO_2CH_2Ph$ |
| Cl | Cl | H | $CONMe_2$ |
| Cl | Cl | H | R1 |
| Cl | Cl | H | R2 |
| Cl | Cl | H | R3 |
| Cl | Cl | H | R4 |
| Cl | Cl | H | R5 |
| Cl | Cl | H | R6 |
| Cl | Cl | H | R7 |
| Cl | Cl | H | R8 |
| Cl | Cl | H | R9 |
| Cl | Cl | H | R10 |
| Cl | Cl | H | R11 |
| Cl | Cl | H | R12 |
| Cl | Cl | H | R13 |
| Cl | Cl | H | R14 |
| Cl | Cl | H | R15 |
| Cl | Cl | H | R16 |
| Cl | Cl | H | R17 |
| Cl | Cl | H | R18 |
| Cl | Cl | H | R19 |
| Cl | Cl | H | R20 |
| Cl | Cl | H | R21 |
| Cl | Cl | H | R22 |
| Cl | Cl | H | R23 |
| Cl | Cl | H | R24 |
| Cl | Cl | H | R25 |
| Cl | Cl | H | R26 |
| Cl | Cl | H | R27 |
| Cl | Cl | H | R28 |
| Cl | Cl | H | R29 |
| Cl | Cl | H | R30 |
| Cl | Cl | H | R31 |
| Cl | Cl | H | R32 |
| Cl | Cl | H | R33 |
| Cl | Cl | H | R34 |
| Cl | Cl | H | R35 |
| Cl | Cl | H | Me |
| Cl | Cl | H | $CH_2Ph$ |
| Cl | Cl | H | $SO_2Me$ |
| Cl | Cl | H | $SO_2Et$ |
| Cl | Cl | H | $SO_2nPr$ |
| Cl | Cl | H | $SO_2iPr$ |
| Cl | Cl | H | R36 |
| Cl | Br | H | $CO_2tBu$ |
| Cl | Br | H | COMe |
| Cl | Br | H | COtBu |
| Cl | F | H | COtBu |
| Cl | F | H | COMe |
| Cl | F | H | COtBu |
| Cl | I | H | COtBu |
| Cl | I | H | COMe |
| Cl | I | H | COPh |
| Cl | CN | H | COtBu |
| Cl | CN | H | COMe |
| Cl | CN | H | COPh |
| Cl | $CO_2Me$ | H | COtBu |
| Cl | $CO_2Me$ | H | COMe |
| Cl | $CO_2Me$ | H | COPh |
| Cl | $CO_2Et$ | H | COtBu |
| Cl | $CO_2Et$ | H | COMe |
| Cl | $CO_2Et$ | H | COPh |
| Cl | Et | H | COtBu |
| Cl | Et | H | COMe |
| Cl | Et | H | COPh |
| Cl | iPr | H | COtBu |
| Cl | iPr | H | COMe |
| Cl | iPr | H | COPh |
| Cl | $CH_2CF_3$ | H | COtBu |
| Cl | $CH_2CF_3$ | H | COMe |
| Cl | $CH_2CF_3$ | H | COPh |
| Cl | OMe | H | COtBu |
| Cl | OMe | H | COMe |
| Cl | OMe | H | COPh |
| Cl | OEt | H | COtBu |

TABLE 2-continued

| | | | |
|---|---|---|---|
| Cl | OEt | H | COMe |
| Cl | OEt | H | COPh |
| Cl | OiPr | H | COtBu |
| Cl | OiPr | H | COMe |
| Cl | OiPr | H | COPh |
| Cl | $OCF_3$ | H | COtBu |
| Cl | $OCF_3$ | H | COMe |
| Cl | $OCF_3$ | H | COPh |
| Cl | OPh | H | COtBu |
| Cl | OPh | H | COMe |
| Cl | OPh | H | COPh |
| Cl | F | F | COtBu |
| Cl | F | F | COMe |
| Cl | F | F | COEt |
| Cl | F | F | COnPr |
| Cl | F | F | COnBu |
| Cl | F | F | COPh |
| Cl | F | F | $COCCl_3$ |
| Cl | F | F | $COCF_3$ |
| Cl | F | F | $CO_2Me$ |
| Cl | F | F | $CO_2nBu$ |
| Cl | F | F | $CO_2CH_2Ph$ |
| Cl | F | F | $CONMe_2$ |
| Cl | F | F | R1 |
| Cl | F | F | R2 |
| Cl | F | F | R3 |
| Cl | F | F | R4 |
| Cl | F | F | R5 |
| Cl | F | F | R6 |
| Cl | F | F | R7 |
| Cl | F | F | R8 |
| Cl | F | F | R9 |
| Cl | F | F | R10 |
| Cl | F | F | R11 |
| Cl | F | F | R12 |
| Cl | F | F | R13 |
| Cl | F | F | R14 |
| Cl | F | F | R15 |
| Cl | F | F | R16 |
| Cl | F | F | R17 |
| Cl | F | F | R18 |
| Cl | F | F | R19 |
| Cl | F | F | R20 |
| Cl | F | F | R21 |
| Cl | F | F | R22 |
| Cl | F | F | R23 |
| Cl | F | F | R24 |
| Cl | F | F | R25 |
| Cl | F | F | R26 |
| Cl | F | F | R27 |
| Cl | F | F | R28 |
| Cl | F | F | R29 |
| Cl | F | F | R30 |
| Cl | F | F | R31 |
| Cl | F | F | R32 |
| Cl | F | F | R33 |
| Cl | F | F | R34 |
| Cl | F | F | R35 |
| Cl | F | F | Me |
| Cl | F | F | $CH_2Ph$ |
| Cl | F | F | $SO_2Me$ |
| Cl | F | F | $SO_2Et$ |
| Cl | F | F | $SO_2nPr$ |
| Cl | F | F | $SO_2iPr$ |
| Cl | F | F | R36 |
| Cl | F | Me | COtBu |
| Cl | F | Me | COMe |
| Cl | F | Me | COEt |
| Cl | F | Me | COnPr |
| Cl | F | Me | COnBu |
| Cl | F | Me | COPh |
| Cl | F | Me | $COCCl_3$ |
| Cl | F | Me | $COCF_3$ |
| Cl | F | Me | $CO_2Me$ |
| Cl | F | Me | $CO_2nBu$ |
| Cl | F | Me | $CO_2CH_2Ph$ |
| Cl | F | Me | $CONMe_2$ |
| Cl | F | Me | R1 |
| Cl | F | Me | R2 |
| Cl | F | Me | R3 |
| Cl | F | Me | R4 |
| Cl | F | Me | R5 |
| Cl | F | Me | R6 |
| Cl | F | Me | R7 |
| Cl | F | Me | R8 |
| Cl | F | Me | R9 |
| Cl | F | Me | R10 |
| Cl | F | Me | R11 |
| Cl | F | Me | R12 |
| Cl | F | Me | R13 |
| Cl | F | Me | R14 |
| Cl | F | Me | R15 |
| Cl | F | Me | R16 |
| Cl | F | Me | R17 |
| Cl | F | Me | R18 |
| Cl | F | Me | R19 |
| Cl | F | Me | R20 |
| Cl | F | Me | R21 |
| Cl | F | Me | R22 |
| Cl | F | Me | R23 |
| Cl | F | Me | R24 |
| Cl | F | Me | R25 |
| Cl | F | Me | R26 |
| Cl | F | Me | R27 |
| Cl | F | Me | R28 |
| Cl | F | Me | R29 |
| Cl | F | Me | R30 |
| Cl | F | Me | R31 |
| Cl | F | Me | R32 |
| Cl | F | Me | R33 |
| Cl | F | Me | R34 |
| Cl | F | Me | R35 |
| Cl | F | Me | Me |
| Cl | F | Me | $CH_2Ph$ |
| Cl | F | Me | $SO_2Me$ |
| Cl | F | Me | $SO_2Et$ |
| Cl | F | Me | $SO_2nPr$ |
| Cl | F | Me | $SO_2iPr$ |
| Cl | F | Me | R36 |
| Cl | F | Cl | COtBu |
| Cl | F | Cl | COMe |
| Cl | F | Cl | COEt |
| Cl | F | Cl | COnPr |
| Cl | F | Cl | COnBu |
| Cl | F | Cl | COPh |
| Cl | F | Cl | $COCCl_3$ |
| Cl | F | Cl | $COCF_3$ |
| Cl | F | Cl | $CO_2Me$ |
| Cl | F | Cl | $CO_2nBu$ |
| Cl | F | Cl | $CO_2CH_2Ph$ |
| Cl | F | Cl | $CONMe_2$ |
| Cl | F | Cl | R1 |
| Cl | F | Cl | R2 |
| Cl | F | Cl | R3 |
| Cl | F | Cl | R4 |
| Cl | F | Cl | R5 |
| Cl | F | Cl | R6 |
| Cl | F | Cl | R7 |
| Cl | F | Cl | R8 |
| Cl | F | Cl | R9 |
| Cl | F | Cl | R10 |
| Cl | F | Cl | R11 |
| Cl | F | Cl | R12 |
| Cl | F | Cl | R13 |
| Cl | F | Cl | R14 |
| Cl | F | Cl | R15 |
| Cl | F | Cl | R16 |
| Cl | F | Cl | R17 |
| Cl | F | Cl | R18 |
| Cl | F | Cl | R19 |
| Cl | F | Cl | R20 |
| Cl | F | Cl | R21 |
| Cl | F | Cl | R22 |
| Cl | F | Cl | R23 |
| Cl | F | Cl | R24 |
| Cl | F | Cl | R25 |
| Cl | F | Cl | R26 |
| Cl | F | Cl | R27 |

TABLE 2-continued

| | | | |
|---|---|---|---|
| Cl | F | Cl | R28 |
| Cl | F | Cl | R29 |
| Cl | F | Cl | R30 |
| Cl | F | Cl | R31 |
| Cl | F | Cl | R32 |
| Cl | F | Cl | R33 |
| Cl | F | Cl | R34 |
| Cl | F | Cl | R35 |
| Cl | F | Cl | Me |
| Cl | F | Cl | CH$_2$Ph |
| Cl | F | Cl | SO$_2$Me |
| Cl | F | Cl | SO$_2$Et |
| Cl | F | Cl | SO$_2$nPr |
| Cl | F | Cl | SO$_2$iPr |
| Cl | F | Cl | R36 |
| Cl | F | OMe | COtBu |
| Cl | F | OMe | COMe |
| Cl | F | OMe | COPh |
| Cl | F | CF$_3$ | COtBu |
| Cl | F | CF$_3$ | COMe |
| Cl | F | CF$_3$ | COPh |
| Cl | Cl | Cl | COtBu |
| Cl | Cl | Cl | COMe |
| Cl | Cl | Cl | COPh |
| Cl | Cl | Me | COtBu |
| Cl | Cl | Me | COMe |
| Cl | Cl | Me | COPh |
| Cl | Me | Me | COtBu |
| Cl | Me | Me | COMe |
| Cl | Me | Me | COPh |
| Cl | OMe | OMe | COtBu |
| Cl | OMe | OMe | COMe |
| Cl | OMe | OMe | COPh |
| Et | CF$_3$ | H | COtBu |
| Et | Me | H | COtBu |
| Et | Cl | H | COtBu |
| Et | F | F | COtBu |
| Et | F | Me | COtBu |
| Et | F | Cl | COtBu |
| nPr | CF$_3$ | H | COtBu |
| nPr | Me | H | COtBu |
| nPr | Cl | H | COtBu |
| nPr | F | F | COtBu |
| nPr | F | Me | COtBu |
| nPr | F | Cl | COtBu |
| iPr | CF$_3$ | H | COtBu |
| iPr | Me | H | COtBu |
| iPr | Cl | H | COtBu |
| iPr | F | F | COtBu |
| iPr | F | Me | COtBu |
| iPr | F | Cl | COtBu |
| nBu | CF$_3$ | H | COtBu |
| nBu | Me | H | COtBu |
| nBu | Cl | H | COtBu |
| nBu | F | F | COtBu |
| nBu | F | Me | COtBu |
| nBu | F | Cl | COtBu |
| tBu | CF$_3$ | H | COtBu |
| tBu | Me | H | COtBu |
| tBu | Cl | H | COtBu |
| tBu | F | F | COtBu |
| tBu | F | Me | COtBu |
| tBu | F | Cl | COtBu |
| nHex | CF$_3$ | H | COtBu |
| nHex | Me | H | COtBu |
| nHex | Cl | H | COtBu |
| nHex | F | F | COtBu |
| nHex | F | Me | COtBu |
| nHex | F | Cl | COtBu |
| cHex | CF$_3$ | H | COtBu |
| cHex | Me | H | COtBu |
| cHex | Cl | H | COtBu |
| cHex | F | F | COtBu |
| cHex | F | Me | COtBu |
| cHex | F | Cl | COtBu |
| Ph | CF$_3$ | H | COtBu |
| Ph | Me | H | COtBu |
| Ph | Cl | H | COtBu |
| Ph | F | F | COtBu |
| Ph | F | Me | COtBu |
| Ph | F | Cl | COtBu |
| CF$_3$ | CF$_3$ | H | COtBu |
| CF$_3$ | Me | H | COtBu |
| CF$_3$ | Cl | H | COtBu |
| CF$_3$ | F | F | COtBu |
| CF$_3$ | F | Me | COtBu |
| CF$_3$ | F | Cl | COtBu |
| CH$_2$CF$_3$ | CF$_3$ | H | COtBu |
| CH$_2$CF$_3$ | Me | H | COtBu |
| CH$_2$CF$_3$ | Cl | H | COtBu |
| CH$_2$CF$_3$ | F | F | COtBu |
| CH$_2$CF$_3$ | F | Me | COtBu |
| CH$_2$CF$_3$ | F | Cl | COtBu |
| OMe | CF$_3$ | H | COtBu |
| OMe | Me | H | COtBu |
| OMe | Cl | H | COtBu |
| OMe | F | F | COtBu |
| OMe | F | Me | COtBu |
| OMe | F | Cl | COtBu |
| OEt | CF$_3$ | H | COtBu |
| OEt | Me | H | COtBu |
| OEt | Cl | H | COtBu |
| OEt | F | F | COtBu |
| OEt | F | Me | COtBu |
| OEt | F | Cl | COtBu |
| OiPr | CF$_3$ | H | COtBu |
| OiPr | Me | H | COtBu |
| OiPr | Cl | H | COtBu |
| OiPr | F | F | COtBu |
| OiPr | F | Me | COtBu |
| OiPr | F | Cl | COtBu |
| OtBu | CF$_3$ | H | COtBu |
| OtBu | Me | H | COtBu |
| OtBu | Cl | H | COtBu |
| OtBu | F | F | COtBu |
| OtBu | F | Me | COtBu |
| OtBu | F | Cl | COtBu |
| OPh | CF$_3$ | H | COtBu |
| OPh | Me | H | COtBu |
| OPh | Cl | H | COtBu |
| OPh | F | F | COtBu |
| OPh | F | Me | COtBu |
| OPh | F | Cl | COtBu |
| OCF$_3$ | CF$_3$ | H | COtBu |
| OCF$_3$ | Me | H | COtBu |
| OCF$_3$ | Cl | H | COtBu |
| OCF$_3$ | F | F | COtBu |
| OCF$_3$ | F | Me | COtBu |
| OCF$_3$ | F | Cl | COtBu |
| CN | CF$_3$ | H | COtBu |
| CN | Me | H | COtBu |
| CN | Cl | H | COtBu |
| CN | F | F | COtBu |
| CN | F | Me | COtBu |
| CN | F | Cl | COtBu |
| NO$_2$ | CF$_3$ | H | COtBu |
| NO$_2$ | Me | H | COtBu |
| NO$_2$ | Cl | H | COtBu |
| NO$_2$ | F | F | COtBu |
| NO$_2$ | F | Me | COtBu |
| NO$_2$ | F | Cl | COtBu |
| F | CH$_2$F | H | COtBu |
| F | CH$_2$F | H | COMe |
| F | CH$_2$F | H | COEt |
| F | CH$_2$F | H | COnPr |
| F | CH$_2$F | H | COCF$_3$ |
| F | CH$_2$F | H | COPh |
| F | CH$_2$F | H | CO$_2$Me |
| F | CH$_2$F | H | CO$_2$nBu |
| F | CH$_2$F | H | R1 |
| F | CH$_2$F | H | R2 |
| F | CH$_2$F | H | R3 |
| F | CH$_2$F | H | R13 |
| F | CH$_2$F | H | R14 |
| F | CH$_2$F | H | R19 |
| F | CH$_2$F | H | R24 |
| F | CH$_2$F | H | R25 |
| F | CH$_2$F | H | R26 |

TABLE 2-continued
| F | CH$_2$F | H | R27 |
| F | CH$_2$F | H | R28 |
| F | CH$_2$F | H | R29 |
| F | CH$_2$F | H | R30 |
| F | CH$_2$F | H | R31 |
| F | CH$_2$F | H | R32 |
| F | CH$_2$F | H | R35 |
| F | CH$_2$F | H | Me |
| F | CH$_2$F | H | CH$_2$Ph |
| F | CH$_2$F | H | SO$_2$Me |
| F | CH$_2$F | H | SO$_2$Et |
| F | CH$_2$F | H | SO$_2$nPr |
| F | CH$_2$F | H | R36 |
TABLE 3
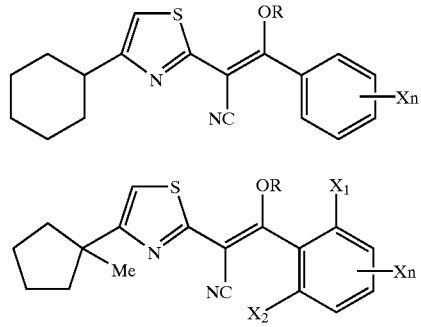
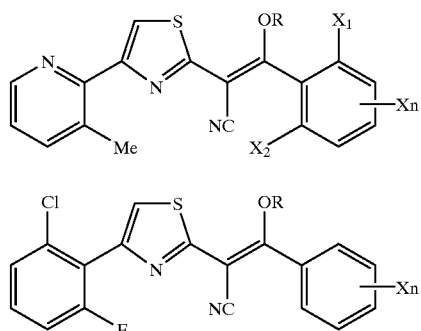
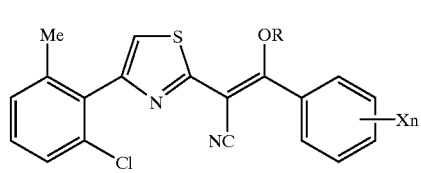
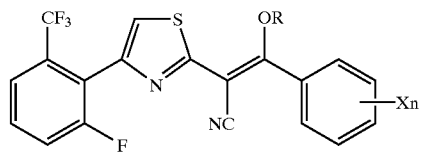
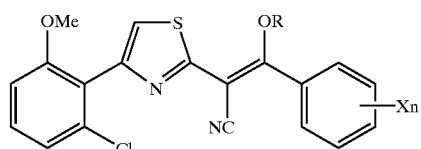
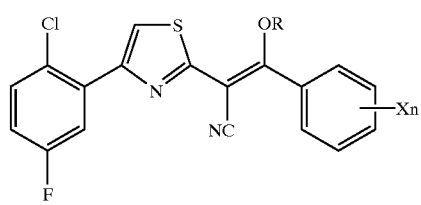
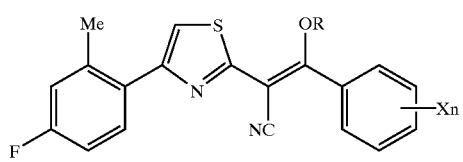

TABLE 3-continued

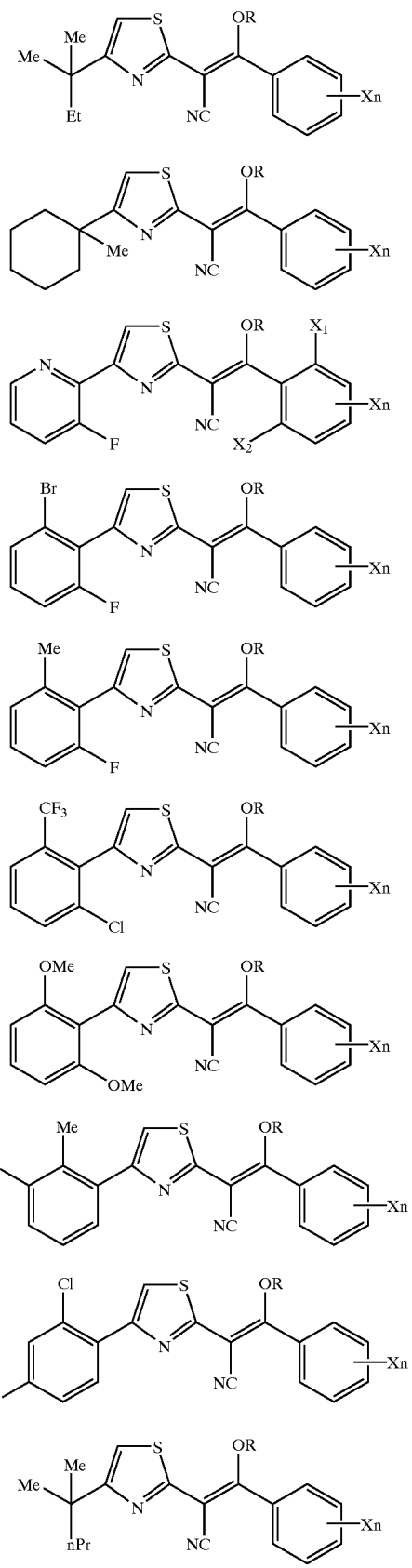

TABLE 3-continued

| Xn | R | Xn | R |
|---|---|---|---|
| 2-CF$_3$-3,4-F$_2$ | COtBu | 2,3,5-F$_3$ | COtBu |
| 2-CF$_3$-3,4-F$_2$ | R1 | 2,3,5-F$_3$ | R1 |
| 2-CF$_3$-3,4-F$_2$ | R2 | 2,3,5-F$_3$ | R2 |
| 2-CF$_3$-3,5-F$_2$ | COtBu | 2,3,6-F$_3$ | COtBu |
| 2-CF$_3$-3,5-F$_2$ | R1 | 2,3,6-F$_3$ | R1 |
| 2-CF$_3$-3,5-F$_2$ | R2 | 2,3,6-F$_3$ | R2 |
| 2-CF$_3$-3,6-F$_2$ | COtBu | 2,4,5-F$_3$ | COtBu |
| 2-CF$_3$-3,6-F$_2$ | R1 | 2,4,5-F$_3$ | R1 |
| 2-CF$_3$-3,6-F$_2$ | R2 | 2,4,5-F$_3$ | R2 |
| 2-CF$_3$-4,5-F$_2$ | COtBu | 2,4,6-F$_3$ | COtBu |
| 2-CF$_3$-4,5-F$_2$ | R1 | 2,4,6-F$_3$ | R1 |
| 2-CF$_3$-4,5-F$_2$ | R2 | 2,4,6-F$_3$ | R2 |
| 2-CF$_3$-4,6-F$_2$ | COtBu | 2-Cl-3,4-F$_2$ | COtBu |
| 2-CF$_3$-4,6-F$_2$ | R1 | 2-Cl-3,4-F$_2$ | R1 |
| 2-CF$_3$-4,6-F$_2$ | R2 | 2-Cl-3,4-F$_2$ | R2 |
| 2-CF$_3$-5,6-F$_2$ | COtBu | 2-Cl-3,5-F$_2$ | COtBu |
| 2-CF$_3$-5,6-F$_2$ | R1 | 2-Cl-3,5-F$_2$ | R1 |
| 2-CF$_3$-5,6-F$_2$ | R2 | 2-Cl-3,5-F$_2$ | R2 |
| 2-Me-3,4-F$_2$ | COtBu | 2-Cl-3,6-F$_2$ | COtBu |
| 2-Me-3,4-F$_2$ | R1 | 2-Cl-3,6-F$_2$ | R1 |
| 2-Me-3,4-F$_2$ | R2 | 2-Cl-3,6-F$_2$ | R2 |
| 2-Me-3,5-F$_2$ | COtBu | 2-Cl-4,5-F$_2$ | COtBu |
| 2-Me-3,5-F$_2$ | R1 | 2-Cl-4,5-F$_2$ | R1 |
| 2-Me-3,5-F$_2$ | R2 | 2-Cl-4,5-F$_2$ | R2 |
| 2-Me-3,6-F$_2$ | COtBu | 2-Cl-4,6-F$_2$ | COtBu |
| 2-Me-3,6-F$_2$ | R1 | 2-Cl-4,6-F$_2$ | R1 |
| 2-Me-3,6-F$_2$ | R2 | 2-Cl-4,6-F$_2$ | R2 |
| 2-Me-4,5-F$_2$ | COtBu | 2-Cl-5,6-F$_2$ | COtBu |
| 2-Me-4,5-F$_2$ | R1 | 2-Cl-5,6-F$_2$ | R1 |
| 2-Me-4,5-F$_2$ | R2 | 2-Cl-5,6-F$_2$ | R2 |
| 2-Me-4,6-F$_2$ | COtBu | 2-CF$_3$-3,4,6-F$_3$ | COtBu |
| 2-Me-4,6-F$_2$ | R1 | 2-CF$_3$-3,5,6-F$_3$ | COtBu |
| 2-Me-4,6-F$_2$ | R2 | 2-CF$_3$-4-Cl-6-F | COtBu |
| 2-Me-5,6-F$_2$ | COtBu | 2-Me-3,4,6-F$_3$ | COtBu |
| 2-Me-5,6-F$_2$ | R1 | 2-Me-3,5,6-F$_3$ | COtBu |
| 2-Me-5,6-F$_2$ | R2 | 2,3,4,5,6-F$_3$ | COtBu |
| 2,3,4-F$_3$ | COtBu | 2-OMe-4,5-F$_2$ | COtBu |
| 2,3,4-F$_3$ | R1 | 2-OMe-4,5-Cl$_2$ | COtBu |
| 2,3,4-F$_3$ | R2 | | |

TABLE 4

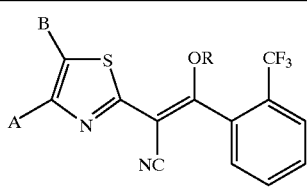

TABLE 4-continued
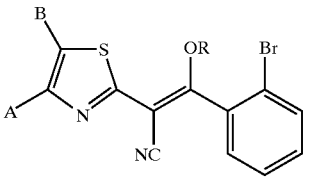
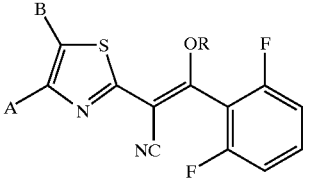
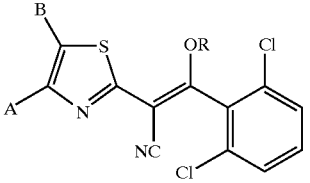
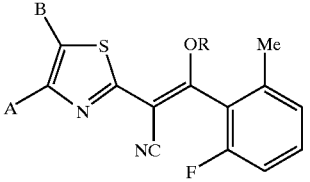
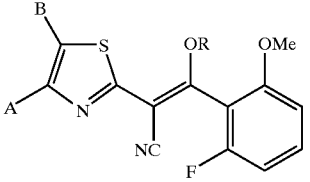
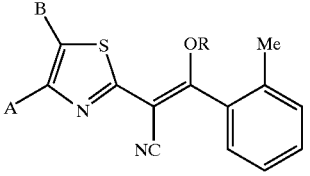
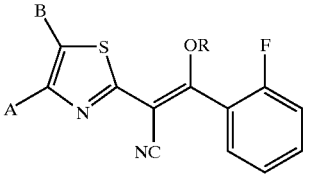
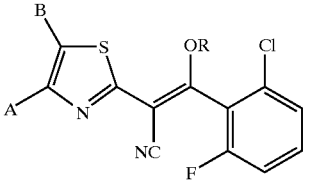
TABLE 4-continued
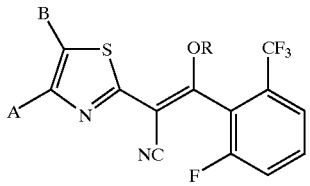
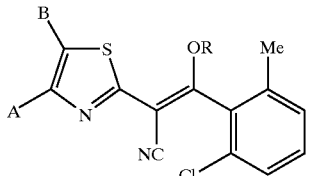
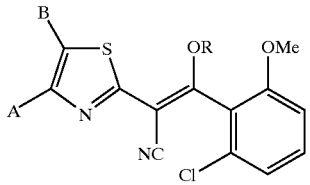
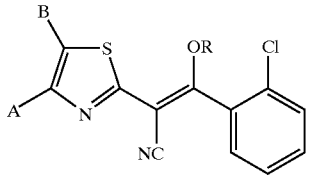
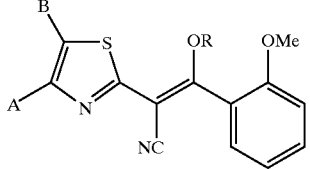
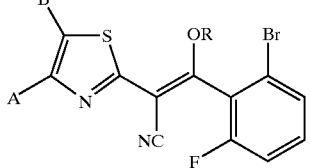
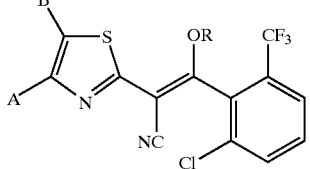
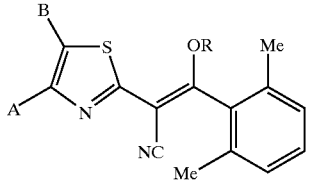

TABLE 4-continued

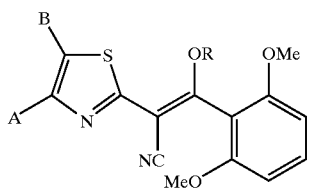

| A | B | R |
|---|---|---|
| 2-CF₃-3-F—Ph | H | COtBu |
| 2-CF₃-4-F—Ph | H | COtBu |
| 2-CF₃-5-F—Ph | H | COtBu |
| 2-F-3-Me—Ph | H | COtBu |
| 2-F-4-Me—Ph | H | COtBu |
| 2-F-5-Me—Ph | H | COtBu |
| 2-F-3-Cl—Ph | H | COtBu |
| 2-F-4-Cl—Ph | H | COtBu |
| 2-F-5-Cl—Ph | H | COtBu |
| 2-Br-3-F—Ph | H | COtBu |
| 2-Br-4-F—Ph | H | COtBu |
| 2-Br-5-F—Ph | H | COtBu |
| 2-OMe-3-F—Ph | H | COtBu |
| 2-OMe-4-F—Ph | H | COtBu |
| 2-OMe-5-F—Ph | H | COtBu |
| 2-OMe-3-Cl—Ph | H | COtBu |
| 2-OMe-4-Cl—Ph | H | COtBu |
| 2-OMe-5-Cl—Ph | H | COtBu |
| 2-CF₃-3,4-F₂—Ph | H | COtBu |
| 2-CF₃-3,5-F₂—Ph | H | COtBu |
| 2-CF₃-3,6-F₂—Ph | H | COtBu |
| 2-CF₃-4,5-F₂—Ph | H | COtBu |
| 2-CF₃-4,6-F₂—Ph | H | COtBu |
| 2-CF₃-5,6-F₂—Ph | H | COtBu |
| 2-Me-3,4-F₂—Ph | H | COtBu |
| 2-Me-3,5-F₂—Ph | H | COtBu |
| 2-Me-3,6-F₂—Ph | H | COtBu |
| 2-Me-4,5-F₂—Ph | H | COtBu |
| 2-Me-4,6-F₂—Ph | H | COtBu |
| 2-Me-5,6-F₂—Ph | H | COtBu |
| 2-Cl-3,4-F₂—Ph | H | COtBu |
| 2-Cl-3,5-F₂—Ph | H | COtBu |
| 2-Cl-3,6-F₂—Ph | H | COtBu |
| 2-Cl-4,5-F₂—Ph | H | COtBu |
| 2-Cl-4,6-F₂—Ph | H | COtBu |
| 2-Cl-5,6-F₂—Ph | H | COtBu |
| 2-CF₃-3,4,6-F₃—Ph | H | COtBu |
| 2-CF₃-3,5,6-F₃—Ph | H | COtBu |
| 2-CF₃-4-Cl-6-F—Ph | H | COtBu |
| 2-Me-3,4,6-F₃—Ph | H | COtBu |
| 2-Me-3,5,6-F₃—Ph | H | COtBu |
| 2-OMe-4,5-F₂—Ph | H | COtBu |
| 2-OMe-4,5-Cl₂—Ph | H | COtBu |
| 2-Me-cHex | H | COtBu |
| 2-Me-cHex | H | R1 |
| 2-Me-cHex | H | R2 |
| Me | H | COtBu |
| Me | H | R1 |
| Me | H | R2 |
| Et | H | COtBu |
| Et | H | R1 |
| Et | H | R2 |
| iPr | H | COtBu |
| Pr | H | R1 |
| Pr | H | R2 |
| nPr | H | COtBu |
| nPr | H | R1 |
| nPr | H | R2 |
| nBu | H | COtBu |
| nBu | H | R1 |
| nBu | H | R2 |
| nPen | H | COtBu |
| nPen | H | R1 |
| nPen | H | R2 |
| nHex | H | COtBu |
| nHex | H | R1 |
| nHex | H | R2 |
| CF₁ | H | COtBu |
| CF₂ | H | R1 |
| CF₃ | H | R2 |
| F | H | COtBu |
| F | H | R1 |
| F | H | R2 |
| F | Cl | COtBu |
| Cl | H | COtBu |
| Cl | H | R1 |
| Cl | H | R2 |
| Cl | H | COtBu |
| Cl | Cl | COtBu |
| OMe | H | COtBu |
| OiPr | H | COtBu |
| OtBu | H | COtBu |
| OPh | H | COtBu |
| OCF₃ | H | COtBu |
| 2-pyridyl | H | COtBu |
| 2-pyridyl | H | R1 |
| 2-pyridyl | H | R2 |
| 3-pyridyl | H | COtBu |
| 3-pyridyl | H | R1 |
| 3-pyridyl | H | R2 |
| 4-pyridyl | H | COtBu |
| 4-pyridyl | H | R1 |
| 4-pyridyl | H | R2 |
| 2-thienyl | H | COtBu |
| 2-thienyl | H | R1 |
| 2-thienyl | H | R2 |
| 2-Me—Ph | Me | COtBu |
| 2,6-F₂—Ph | Me | COtBu |
| 2-F-6-CF₁—Ph | Me | COtBu |
| 2-F-6-Me—Ph | Me | COtBu |
| 2-Cl-6-F—Ph | Me | COtBu |
| tBu | Me | COtBu |
| 2-Me—Ph | Et | COtBu |
| 2,6-F₂—Ph | Et | COtBu |
| 2-F-6-CF₄—Ph | Et | COtBu |
| 2-F-6-Me—Ph | Et | COtBu |
| 2-Cl-6-F—Ph | Et | COtBu |
| tBu | Et | COtBu |
| 2-Me—Ph | iPr | COtBu |
| 2,6-F₂—Ph | iPr | COtBu |
| 2-F-6-CF₃—Ph | iPr | COtBu |
| 2-F-6-Me—Ph | iPr | COtBu |
| 2-Cl-6-F—Ph | iPr | COtBu |
| tBu | iPr | COtBu |
| 2-Me—Ph | Ph | COtBu |
| 2,6-F₂—Ph | Ph | COtBu |
| 2-F-6-CF₃—Ph | Ph | COtBu |
| 2-F-6-Me—Ph | Ph | COtBu |
| 2-Cl-6-F—Ph | Ph | COtBu |
| tBu | Ph | COtBu |
| 2-Me—Ph | CF₃ | COtBu |
| 2,6-F₂—Ph | CF₃ | COtBu |
| 2-F-6-CF₃—Ph | CF₃ | COtBu |
| 2-F-6-Me—Ph | CF₃ | COtBu |
| 2-Cl-6-F—Ph | CF₃ | COtBu |
| tBu | CF₃ | COtBu |
| 2-Me—Ph | cPr | COtBu |
| 2,6-F₂—Ph | cPr | COtBu |
| 2-F-6-CF₁—Ph | cPr | COtBu |
| 2-F-6-Me—Ph | cPr | COtBu |
| 2-Cl-6-F—Ph | cPr | COtBu |
| tBu | cPr | COtBu |
| 2-Me—Ph | cHex | COtBu |
| 2,6-F₂—Ph | cHex | COtBu |
| 2-F-6-CF₃—Ph | cHex | COtBu |
| 2-F-6-Me—Ph | cHex | COtBu |
| 2-Cl-6-F—Ph | cHex | COtBu |
| tBu | cHex | COtBu |
| 2-Me—Ph | F | COtBu |
| 2,6-F₂—Ph | F | COtBu |
| 2-F-6-CF₃—Ph | F | COtBu |
| 2-F-6-Me—Ph | F | COtBu |
| 2-Cl-6-F—Ph | F | COtBu |
| tBu | F | COtBu |
| 2-Me—Ph | Cl | COtBu |
| 2,6-F₂—Ph | Cl | COtBu |

TABLE 4-continued

| | | |
|---|---|---|
| 2-F-6-CF$_3$—Ph | Cl | COtBu |
| 2-F-6-Me—Ph | Cl | COtBu |
| 2-Cl-6-F—Ph | Cl | COtBu |
| tBu | Cl | COtBu |
| 2-Me—Ph | CO$_2$Me | COtBu |
| 2,6-F$_2$—Ph | CO$_2$Me | COtBu |
| 2-F-6-CF$_3$—Ph | CO$_2$Me | COtBu |
| 2-F-6-Me—Ph | CO$_2$Me | COtBu |
| 2-Cl-6-F—Ph | CO$_2$Me | COtBu |
| tBu | CO$_2$Me | COtBu |
| 2-Me—Ph | CO$_3$Et | COtBu |
| 2,6-F$_2$—Ph | CO$_3$Et | COtBu |
| 2-F-6-CF$_3$—Ph | CO$_3$Et | COtBu |
| 2-F-6-Me—Ph | CO$_3$Et | COtBu |
| 2-Cl-6-F—Ph | CO$_3$Et | COtBu |
| tBu | CO$_3$Et | COtBu |
| 2-Me—Ph | CO$_3$tBu | COtBu |
| 2,6-F$_2$—Ph | CO$_3$tBu | COtBu |
| 2-F-6-CF$_3$—Ph | CO$_3$tBu | COtBu |
| 2-F-6-Me—Ph | CO$_3$tBu | COtBu |
| 2-Cl-6-F—Ph | CO$_3$tBu | COtBu |
| tBu | CO$_3$tBu | COtBu |

(Insecticides and Acaricides)

Compositions containing the compounds of the present invention obtained in such ways as those mentioned above are useful, for example, as agricultural and horticultural insecticides, acaricides, sanitary insect pest controlling agents and anti-fouling agents for aqueous adhesive organisms. It is particularly preferable to apply compositions containing the compounds of the present invention as agricultural and horticultural insecticides and acaricides.

The compounds of the present invention can be used in the pure form without adding other ingredients, when they are actually applied as agricultural and horticultural insecticides or acaricides. When applied as agrochemicals, they may be used in forms that general agrochemicals can take, such as wettable powders, granules, dusts, emulsifiable concentrates, water soluble powders, flowable concentrates and flowables.

In order to make solid formulations, vegetable powders such as soybean flour and wheat flour; fine mineral powders such as diatomaceous earth, apatite, gypsum, talc, bentonite, pyrophylite and clay; and organic and inorganic compounds such as sodium benzoate, urea and Glauber's salt can be used as additives and carriers. When the purpose is to prepare liquid formulations, as additives and carriers, petroleum fractions such as kerosene, xylene and solvent naphtha, cyclohexane, cyclohexanone, DMF, DMSO, alcohol, acetone, trichloroethylene, methyl isobutyl ketone, mineral oils, vegetable oils, water and the like can be used as solvents.

It is possible to further add surfactant, if required, to make these formulations homogeneous and stable forms. There are no particular restrictions on surfactant used. Their examples include nonionic surfactant such as polyoxyethylene-added alkylphenyl ethers, polyoxyethylene-added alkyl ethers, polyoxyethylene-added higher fatty acid esters, polyoxyethylene-added sorbitan higher fatty acid esters and polyoxyethylene-added tristylylphenyl ethers; polyoxyethylene-added alkylphenyl ether sulfates, alkylbenzenesulfonates, higher alcohol sulfates, alkylnaphthalene sulfonates, polycarboxylic acid salts, lignin sulfonates, condensation products of alkylnaphthalene sulfonates with formaldehyde, and copolymers of isobutylene and maleic anhydride.

An amount of the active ingredient (a compound of the present invention) in a formulation is preferably 0.01 to 90% by weight, more preferably about 0.05 to 85% by weight.

The obtained wettable powders, emulsifiable concentrates, flowable concentrates and flowables are diluted with water to specified concentrations to use as suspensions or emulsions. The dusts and granules are used as they are to directly spray on plants or soil.

It goes without saying that the compounds of the present invention are sufficiently effective by themselves. They can be used, however, by mixing with one or more of various fungicides, insecticides, acaricides or synergists.

Representative examples of fungicides, insecticides, acaricides and plant growth regulators that can be used to mix with the compounds of the present invention are shown in the following:

Fungicides

Captan, Forpet, Thiuram, Ziram, Zineb, Maneb, Mancozeb, Propineb, Polycarbamate, Chlorotalonyl, Quintozene, Captafol, Iprodione, Prothimidon, Vinclosolin, Fluorimide, Cymoxanil, Mepronyl, Flutoranyl, Penthichlon, Oxycarboxin, Phosethyl-aluminum, Propamocarb, Triazimefon, Triazimenol, Propiconazole, Dichloptrazole, Bitertanol, Hexaconazole, Microbutanil, Flusilazole, Ethaconazole, Fluotrimazole, Flutriafen, Penconazole, Diniconazole, Cyproconazole, Phenalimol, Triflumizole, Prochloraz, Imazaryl, Pefurazoate, Tridemorph, Fenpropymorph, Triforin, Buthiobate, Pryfenox, Anilazine, Polyoxin, Metharaxyl, Oxadixyl, Flaraxyl, Isoprothiorane, Probenazole, Pyrolnitrin, Blasticidin S, Kasugamycin, Validamycin, Sulfric acid dihydrostreptomycin, Benomil, Carbendazim, Thiophanate-methyl, Hymexazole, Basic copper chloride, Basic copper sulfate, Triphenyl tin acetate, Triphenyl tin hydroxide, Diethofencarb, Methasulfocarb, Quinomethionate, Binapacryl, Lecithin, Sodium carbonate, Dithianon, Dinocap, Phenaminosulf, Dichlomezine, Guazatine, Dozin, IBP, Edifenphos, Mepanipyrim, Ferimzone, Trichlamide, Methasulfocarb, Fluazinam, Etokinorakku (oxolinic acid), Dimethomorph, Pyroquiron, Tecrofutaram, Futharide, Phenazinoxyde, Thiabendazole, Tricyclazole, Vinclozolin, Cymoxanil, Cyclobutanyl, Guazatine, Propamocarb-hydrochloride, Oxolinic acid and the like.

Insecticides and Acaricides

Organophosphorus and Carbamate Insecticides

Fenthion, Fenitrothion, Diazinon, Chlorpyrifos, ESP, Vamidothion, Fenthoate, Dimethoate, Formothion, Malathon, Trichlorfon, Thiomethon, Phosmet, Dichlorvos, Acephate, EPBP, Methylparathion, Oxydimethonmethyl, Ethion, Salithion, Cyanophos, Isoxathion, Pyridafenthion, Phosalon, Methidathion, Sulprofos, Chlorfenvinphos, Tetrachlorvinphos, Dimethylvinphos, Propaphos, isofenphos, Ethylthiomethon, Profenofos, Pyrachlofos, Monoclotophos, Adinphosmethyl, Aldicarb, Methomyl, Thiodicarb, Carbofuran, Carbosulfan, Benfuracarb, Furathiocarb, Propoxur, BPMC, MTMC, MIPC, Carbaryl, Pyrimicarb, Ethiofencarb, Fenoxycarb and the like.

Pyrethroid Type Insecticides

Permethrin, Cypermethrin, Deltamethrin, Fenvalerate, Fenpropathrin, Pyrethrin, Allethrin, Tetramethrin, Resmethrin, Dimethrin, Propathrin, Phenothrin, Prothrin, Fulvalinate, Cyfluthrin, Cyhalothrin, Flucythrinate, Ethofenprox, Cycloprothrin, Tralomethrin, Silafluofen, Profenprox, Acrynathrin and the like.

Benzoyl Urea and other Insecticides

Diflubenzuron, Chlorfluazuron, Hexaflumron, Triflumron, Tetrabenzuron, Flufenoxuron, Flucycloxuron, Buprofezin, Pyriproxyfen, Methoprene, Benzoepin (endosulfan), Diafenthiuron, Acetamiprid, Imidacloprid, Nitenpyram, Fipronyl, Caltop, Thiocyclam, Bensultap, Chlorphenapyr, Emanectin-benzoate, Tebufenozide, Nicotine sulfate, Rotenone, Metaldehyde, machine oils, BT, agrochemicals for microbial organisms such as insect disease viruses, and the like.

Nematicides

Phenamiphos, Fosthiazate and the like.

Acaricides

Chlorbenzylate, Phenisobromolate, Dicofol, Amitraz, BPPS, Benzomate, Hexythiazox, Fenbutatin oxide, Polynactins, Quinomethionate, CPCBS, Tetradifon, Abermectin, Milbemectin, Clofentezin, Cyhexatin, Pyridaben, Fenpyroximate, Tebufenpyrad, Pyrimidifen, Phenothiocarb, Dienochlor, Etoxazole, Halfenprox and the like.

Plant Growth Regulators

Gibberellins (for example, gibberellin A3, gibberellin A4 and gibberellin A7), IAA, NAA and the like.

The compound of the present invention can be used to control agricultural pests, sanitary insect pests, stored grain insect pests, cloth insect pests, house insect pests and the like, and have activities of killing adults, nymphs, larvae and eggs. Their representative examples are shown in the following:

Examples of Lepidopterous pest insects include cotton leafworm, cabbage armyworm, black cutworm, common cabbegeworm, cabbage looper, diamond-back, smaller tea tortrix, tea leaf roller, peach fruit moth, oriental fruit moth, citrus leaf miner, tea leaf roller, apple leaf miner, gypsy moth, tea tussock moth, rice stem borer, grass leaf roller, European corn borer, fall webworm, almond moth, Heliothis sp., Helicoverpa sp., Agrotis sp., casemaking clothes moth, codling moth and cotton bollworm.

Examples of Hemipterous pest insects include green peach aphid, cotton aphid, turnip aphid, grain aphid, bean bug, common green stink bug, arrowhead scale, mulberry mealy scale, greenhouse whitefly, tabacco whitefly, pear psylla, Japanese pear lace bug, brown planthopper, small brown planthopper, white-backed planthopper and green rice leafhopper.

Examples of Coleopterous pest insects include striped flea beetle, cucurbit leaf beetle, Colorado potato beetle, rice water weevil, rice weevil, adzuki bean weevil, Japanese beetle, soybean beetle, Diabrotica sp., cigarette beetle, powder post beetle, pine sawyer, white-spotted longicorn beetle, Agriotis sp., 28-spotted ladybeetle, rust-red flour beetle and cotton boll weevil.

Examples of Dipterous pest insects include housefly, *Calliphora lata, Boettcherisca peregrina,* cucurbit fruit fly, citrus fruit fly, seed maggot, rice leaf miner, yellow drosophila, *Stomoxys calcitrans, Culex tritaeniarhynchus, Aedes aegypti* and *Anlopheles hyrcanus.*

Examples of Thysanopterous pest insects include *Thrips palmi* and tea thrips.

Examples of Hymenopterous pest insects include *Monomorium pharaonis,* yellow harnet and cabbage sawfly.

Examples of Orthopterous pest insects include grasshopper.

Examples of Dictyopterous pest insects include German cockroach, American cockroach and Japanese cockroach.

Examples of Isopterous pest insects include Formosan subterranean termite and *Reticulitermes speratus* Kolbe.

Examples of Aphanipterous pest insects include human flea.

Examples of Anoplurous pest insects include human louse.

Examples of mites include two-spotted spider mite, Kanzawa spider mite, citrus red mite, European red mite, citrus rust mite, apple rust mite, Tarsonemus sp., Brevipalpus sp., Eotetranychus sp., Robin bulb mite, common grain mite, *Desmatophagoides farinae, Boophilus microplus* and *Haemaphysallis bispinosa.*

Examples of plant-parasitic nematodes include southern root-knot nematode, root lesion nematode, soybean cyst nematode, rice white-tip nematode and pine wood nematode.

Many pests such as diamond-back, planthoppers, leafhoppers and aphids, and phytophagous mites have developed resistance against organophosphorus pesticides, carbamate insecticides and acaricides. Therefore, the chemicals have had the problem of lack of efficacy. There has been a desire for chemicals effective on pests and mites of resistant strains. The compounds of the present invention are chemicals having excellent insecticidal and acaricidal effects on pests resistant to organophosphorus pesticides, carbamate insecticides or pyrethroid type agents and mites resistant to acaricides, as well as those of sensitive strains.

The compounds of the present invention induce very slight chemical injuries, have low toxicity on fish and warm-blood animals, and are highly safe.

BEST FORMS TO IMPLEMENT THE INVENTION

The present invention is further described in detail in reference to a Reference Example and Examples.

Reference Example 1

Preparation of 2-[4-(2,6-difluorophenyl)-2-thiazolyl]-3-hydroxy-2'-trifluoromethy-cinnamonitrile

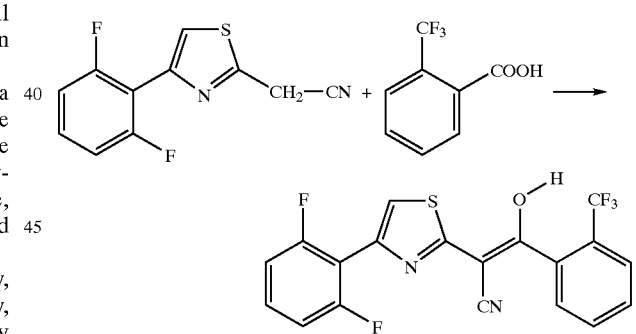

To a solution of 0.8 g (4.2 mmol) of 2-trifluoromethylbenzoic acid in 10 ml of THF was added 0.69 g (4.2 mmol) of carbonylbisimidazole, followed by stirring at room temperature for an hour. To the mixture was added 1.0 g(4.2 mmol) of 2-cyanomethyl-4-(2,6-difluorophenyl)thiazole, and then, 0.17 g (4.2 mmol) of sodium hydride (60% in oil) in an ice-bath. After stirring at room temperature for an hour, another equivalent of sodium hydride (0.17 g, 4.2 mmol: 60% in oil) was added, followed by stirring at room temperature overnight. The reaction mixture was poured into ice-water, acidified with dilute hydrochloric acid, and then, extracted with ethyl acetate. The organic layer was concentrated under diminished pressure, followed by chromatography on silica-gel column (ethyl acetate/n-hexane=1/1, as an eluent) to give 1.1 g(64%) of the title compound. Melting point: 170–172° C.

EXAMPLE 1

Preparation of 2-[4-(2,6-difluorophenyl)-2-thiazolyl]-3-pivaloyloxy-2'-trifluormethyl-cinnamonitrile (Compound No. 3-1)

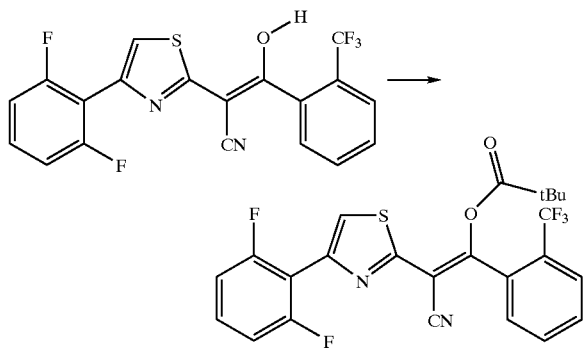

To a solution of 0.6 g (1.5 mmol) of 2-[4-(2,6-difluorophenyl)-2-thiazolyl]-3-hydroxy-2'-trifluoromethylcinnamonitrile in 5 ml of THF were added 0.16 g (1.6 mmol) of triethylamine and 0.2 g (1.6 mmol) of pivaloyl chloride in an ice-bath, respectively, and then, the mixture was stirred at room temperature for 2 hours. After the precipitate was filtered, the filtrate was concentrated under diminished pressure, followed by chromatography on silica-gel column (ethyl acetate/n-hexane=1/4, as an eluent) to give 0.28 g (39%). Melting point: 163–165° C.

Representative examples of the compounds of the present invention that were prepared in such ways as described above are shown in Table 5. The NMR data of oily substances and others are in Table 6.

The symbols used in the tables have the same meanings as those for Tables 1 to 4.

TABLE 5

| Compound No. | A | B | R | Xn | Physical constant* |
|---|---|---|---|---|---|
| 5-1 | 2,6-F$_2$—Ph | H | COtBu | 2-CF$_3$ | [163–165] a |
| 5-2 | 2,6-F$_2$—Ph | H | COMe | 2-CF$_3$ | [165–167] a |
| 5-3 | 2,6-F$_2$—Ph | H | COPh | 2-CF$_3$ | [135–136] |
| 5-4 | 2,6-F$_2$—Ph | H | COtBu | 2-Me | [111–121] |
| 5-5 | 2,6-F$_2$—Ph | H | COMe | 2-Me | [120–128] |
| 5-6 | 2,6-F$_2$—Ph | H | COPh | 2-Me | [182–183.5] a |
| 5-7 | 2,6-F$_2$—Ph | H | R35 | 2-Me | Viscous oil |
| 5-8 | 2,6-F$_2$—Ph | H | COtBu | 2-Cl | [143–146] |
| 5-9 | 2,6-F$_2$—Ph | H | COtBu | 2,6-F | [141–143.5] |
| 5-10 | 2,6-F$_2$—Ph | H | COtBu | 2-Cl-6-F | n$_D^{20.4}$ 1.5726 |
| 5-11 | 2,6-F$_2$—Ph | H | COtBu | 2-F-6-CF$_3$ | Viscous oil |
| 5-12 | 2,6-F$_2$—Ph | H | COtBu | 2-Br | [119–122] |
| 5-13 | 2,6-F$_2$—Ph | H | COtBu | 2-OMe | [72–74] |
| 5-14 | 2,6-F$_2$—Ph | H | COtBu | 2,3-F$_2$—6-CF$_3$ | [142–144] |
| 5-15 | 2-F—Ph | H | COtBu | 2-CF$_3$ | Viscous oil |
| 5-16 | 3-F—Ph | H | COtBu | 2-CF$_3$ | Viscous oil |
| 5-17 | 4-F—Ph | H | COtBu | 2-CF$_3$ | Viscous oil |
| 5-18 | 2-Cl—Ph | H | COtBu | 2-CF$_3$ | Viscous oil |
| 5-19 | 3-Cl—Ph | H | COtBu | 2-CF$_3$ | Viscous oil |
| 5-20 | tBu | H | COtBu | 2-CF$_3$ | n$_D^{20.9}$ 1.5193 |
| 5-21 | tBu | H | COtBu | 2,6-F$_2$ | Viscous oil |
| 5-22 | tBu | H | COtBu | 2,3-F$_2$-6-CF$_3$ | [181–183] |
| 5-23 | cHex | H | R34 | 2-Me | [128–129.5] |
| 5-24 | 2,6-F$_2$—Ph | H | COcPr | 2-Me | [146–148] |
| 5-25 | 2,6-F$_2$—Ph | H | COiPr | 2-Me | [137–139] |
| 5-26 | 2,6-F$_2$—Ph | H | R1 | 2-Me | [120–122] |
| 5-27 | 2,6-F$_2$—Ph | H | CO$_2$nPr | 2-Me | Viscous oil |
| 5-28 | 2,6-F$_2$—Ph | H | CO$_2$CH$_2$Ph | 2-Me | Viscous oil |
| 5-29 | 2,6-F$_2$—Ph | H | SO$_2$nPr | 2-CF$_3$ | [115–119] |
| 5-30 | 2,6-F$_2$—Ph | H | SO$_2$Me | 2-Me | [163–165] |
| 5-31 | 2,6-F$_2$—Ph | H | SO$_2$nPr | 2-Me | Viscous oil |
| 5-32 | 2,6-F$_2$—Ph | H | COtBu | 2-Et | [98.5–99.5] |
| 5-33 | 2,6-F$_2$—Ph | H | COtBu | 2-F | [153–155] |
| 5-34 | 2,6-F$_2$—Ph | H | COtBu | 2-NO$_2$ | Viscous oil |
| 5-35 | 2,6-F$_2$—Ph | H | COtBu | 2-OCF$_3$ | [114–117] |
| 5-36 | 2,6-F$_2$—Ph | H | COtBu | 2-CO$_2$Et | [127–130] |
| 5-37 | 2,6-F$_2$—Ph | H | COtBu | 2,6-Cl$_2$ | [154–159] |
| 5-38 | 2,6-F$_2$—Ph | H | COtBu | 2-Me-3-F | [131–135] |
| 5-39 | 2,6-F$_2$—Ph | H | COtBu | 2-Me-4-F | [131–143] |
| 5-40 | 2,6-F$_2$—Ph | H | COtBu | 2-Me-5-F | [108–109] |
| 5-41 | 2,6-F$_2$—Ph | H | COtBu | 2-Me-6-F | [103–104] |
| 5-42 | 2,6-F$_2$—Ph | Me | COtBu | 2-Me | [140–141] |

TABLE 5-continued

[Structure: thiazole with substituents A, B, and attached to C(CN)=C(OR)-Ph-Xn]

| Compound No. | A | B | R | Xn | Physical constant* |
|---|---|---|---|---|---|
| 5-43 | 2,6-F₂—Ph | Me | COMe | 2-Me | Viscous oil |
| 5-44 | 2-Cl—Ph | H | COtBu | 2-Me | [123–125] |
| 5-45 | 2-Cl—Ph | H | COtBu | 2-Cl | [106–107] |
| 5-46 | 2-Cl—Ph | H | COtBu | 2,6-F₂ | [144–147] |
| 5-47 | 4-Cl—Ph | H | COtBu | 2-CF₃ | Viscous oil |
| 5-48 | 2-CF₃—Ph | H | COtBu | 2-CF₃ | [146–147] |
| 5-49 | 2-CF₃—Ph | H | COtBu | 2-Me | [131–132] |
| 5-50 | 2-CF₃—Ph | H | COtBu | 2,6-F₂ | [86–87] |
| 5-51 | 2-CF₃—Ph | H | COtBu | 2-Cl | [140–141] |
| 5-52 | 2-F—Ph | H | COtBu | 2-Me | [144–145] |
| 5-53 | 2-F—Ph | H | COMe | 2-Me | [127–129] |
| 5-54 | 2-F—Ph | H | COPh | 2-Me | [140–143] |
| 5-55 | 2-F—Ph | H | COtBu | 2-Cl | [143–145] |
| 5-56 | 3-F—Ph | H | COtBu | 2-Me | [129–130] |
| 5-57 | 3-F—Ph | H | COMe | 2-Me | [119–120] |
| 5-58 | 3-F—Ph | H | COPh | 2-Me | [148–149] |
| 5-59 | 3-F—Ph | H | COtBu | 2-Cl | [150–151] |
| 5-60 | 2-Me—Ph | H | COtBu | 2-CF₃ | Viscous oil |
| 5-61 | 2-Me—Ph | H | R31 | 2-Me | [161–164] |
| 5-62 | 2-Me—Ph | H | COtBu | 2-Me | [118–119] |
| 5-63 | 2-Me—Ph | H | COtBu | 2-F | [123–125] |
| 5-64 | 2-Me—Ph | H | COtBu | 2-Cl | $n_D^{20.2}$ 1.5808 |
| 5-65 | 2-Me—Ph | H | COtBu | 2-Br | [99–103] |
| 5-66 | 2-Me—Ph | H | COtBu | 2,6-F₂ | [133–135] |
| 5-67 | 2-Me—Ph | H | COtBu | 2-Cl-6-F | [124–126] |
| 5-68 | 2-Me—Ph | H | COtBu | 2-Me-6-F | [125–129] |
| 5-69 | 3-Me—Ph | H | COtBu | 2-CF₃ | Viscous oil |
| 5-70 | 3-Me—Ph | H | R31 | 2-Me | [130—131] |
| 5-71 | 3-Me—Ph | H | COtBu | 2-Me | Viscous oil |
| 5-72 | 3-Me—Ph | H | COtBu | 2,6-F₂ | [103–105] |
| 5-73 | 2,3-F₂—Ph | H | COtBu | 2-CF₃ | [134–136] |
| 5-74 | 2,3-F₂—Ph | H | COtBu | 2-Me | [101–102] |
| 5-75 | 2,5-F₂—Ph | H | COtBu | 2-CF₃ | [134–136] |
| 5-76 | 2,5-F₂—Ph | H | COtBu | 2-Me | [126–128] |
| 5-77 | 3,5-F₂—Ph | H | COtBu | 2-Me | [114–116] |
| 5-78 | 2,3,6-F₂—Ph | H | COtBu | 2-Me | [105–107] |
| 5-79 | 2-Cl-6-F—Ph | H | COtBu | 2-CF₃ | [150–163] |
| 5-80 | 2-Cl-6-F—Ph | H | COtBu | 2-Me | [121–122] |
| 5-81 | 2-Cl-6-F—Ph | H | COtBu | 2-Cl | [123–126] |
| 5-82 | 2-Cl-6-F—Ph | H | COtBu | 2,6-F₂ | [136–138] |
| 5-83 | 2-Me-3-F—Ph | H | COtBu | 2-Me | [99–104] |
| 5-84 | 2-Me-4-F—Ph | H | COtBu | 2-Me | [139–144] |
| 5-85 | 2-Me-5-F—Ph | H | COtBu | 2-Me | [146–149] |
| 5-86 | 2-Me-5-F—Ph | H | COtBu | 2-Me | [111–116] b |
| 5-87 | 2-Me-6-F—Ph | H | COtBu | 2-CF₃ | [98–101] |
| 5-88 | 2-Me-6-F—Ph | H | COtBu | 2-Me | [109–111] |
| 5-89 | 2-OMe-5-F—Ph | H | COtBu | 2-Me | [148–153] |
| 5-90 | 2-OMe-5-Cl—Ph | H | COtBu | 2-Me | [144–156] |
| 5-91 | 2-OMe-3,5-F₂—Ph | H | COtBu | 2-Me | [134–136] |
| 5-92 | 4-OCF₃—Ph | H | COtBu | 2-CF₃ | Viscous oil |
| 5-93 | 4-OCF₃—Ph | H | COtBu | 2-Me | [123–124] |
| 5-94 | 4-OCF₃—Ph | H | COtBu | 2-Cl | [119–120] |
| 5-95 | Me | H | COtBu | 2-Me | Viscous oil |
| 5-96 | tBu | H | COtBu | 2-Me | [112–113] |
| 5-97 | tBu | H | COMe | 2-Me | $n_D^{21.5}$ 1.5800 |
| 5-98 | tBu | H | R31 | 2-Me | [125–126] |
| 5-99 | 2-pyridyl | H | COtBu | 2-Me | [153–157] |
| 5-100 | 2-thienyl | H | COtBu | 2-Me | [134–138] |
| 5-101 | 2,6-F₂—Ph | H | COtBu | 2-Cl-4-F | [155–157] |
| 5-102 | 2,6-F₂—Ph | H | COtBu | 2-F-6-OMe | [153–155] |
| 5-103 | 1-Me-cHex | H | COtBu | 2-Me | [96–98] |
| 5-104 | 1-Me-cHex | H | COtBu | 2-CF₃ | [92–93] |
| 5-105 | 2-Me-cHex | H | COtBu | 2-Me | [92–94] |
| 5-106 | 2-Me-cHex | H | COtBu | 2-CF₃ | [82–85] |
| 5-107 | 2,6-F₂—Ph | H | R2 | 2-Me | [96–98] |
| 5-108 | 2,6-F₂—Ph | H | R1 | 2-CF₃ | [156–158] |

TABLE 5-continued

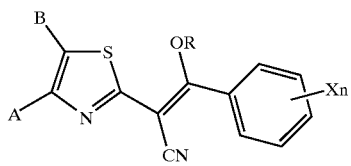

| Compound No. | A | B | R | Xn | Physical constant* |
|---|---|---|---|---|---|
| 5-109 | 2,6-F$_2$—Ph | H | R2 | 2-CF$_3$ | [101–103] |
| 5-110 | cHex | H | COtBu | 2-Me | Viscous oil |

*[ ]: Melting point ° C., and n$_D$: refractive index. These are the same for the following tables.
a: One of isomers. Others are a mixture of isomers.
b: Isomer of Compound No. 5-85.

TABLE 6

NMR Data

| Compound No | $^1$H—NMR (CDCl$_3$, δppm) |
|---|---|
| 5-7 | 1.68 and 1.70(total 6H, 2s), 2.06 and 2.30 (total 3H, 2s), 6.90–7.05(2H, m), 7.10–7.49(m) and 7.59(s) (total 10H) |
| 5-11 | 1.27 and 1.33(total 9H, 2s), 6.83–7.08(2H, m), 7.20–7.70(m) and 7.76(s) (total 5H) |
| 5-15 | 1.29 and 1.32(total 9H, 2s), 6.95–7.12(1H, m), 7.29–7.51(2H, m), 7.63–7.90(6H, m) |
| 5-16 | 1.29 and 1.32(total 9H, 2s), 7.03–7.40(3H, m), 7.62–8.00(m) and 8.33–8.41(m) (total 6H) |
| 5-17 | 1.28 and 1.30(total 9H, 2s), 7.00–7.19(2H, m), 7.60(1H, s), 7.61–7.90(4H, m), 7.93–8.00(2H, m) |
| 5-18 | 1.29 and 1.30(total 9H, 2s), 7.25–7.51(4H, m), 7.61–7.90(4H, m), 8.09 and 8.12(total 1H, 2s) |
| 5-19 | 1.28 and 1.31(total 9H, 2s), 7.30–7.41(2H, m), 7.62–7.90(6H, m), 7.97(1H, bs) |
| 5-21 | 1.10, 1.32, 1.33 and 1.36(total 18H, 4s), 6.89–7.12(total 3H, m), 7.39–7.54(1H, m) |
| 5-27 | 1.92 and 1.96(total 3H, 2s), 1.61–1.79(2H, m), 2.34 and 2.53(total 3H, 2s), 4.17 and 4.18(total 2H, 2t), 6.91–7.00(2H, m), 7.28–7.72(6H, m) |
| 5-28 | 2.48 and 2.49(total 3H, 2s), 5.19 and 5.21(total 2H, 2s), 6.92–7.70(13H, m) |
| 5-31 | 1.96(3H, t), 1.81–1.98(2H, m), 2.53(3H, s), 2.99 (2H, dd), 6.97–7.08(2H, m), 7.28–7.62(5H, m), 7.76(1H, bs) |
| 5-34 | 1.23 and 1.29(total 9H, 2s), 6.90 and 7.01(total total 2H, 2t), 7.20–7.40(1H, m), 7.51–7.95(4H, m), 8.20–8.28(1H, m) |
| 5-43 | 2.19, 2.28, 2.33, 2.35, 2.44 and 2.50(total 9H, 6s), 6.92–7.12(2H, m), 7.27–7.58(5H, m) |
| 5-47 | 1.30 and 1.34(total 9H, 2s), 7.15–7.46 and 7.59–7.96(total 9H, 2m) |
| 5-60 | 1.29 and 1.32(total 9H, 2s), 2.32 and 2.50(total 3H, 2s), 7.15–7.33(4H, m), 7.48–7.91(5H, m) |
| 5-69 | 1.30 and 1.33(total 9H, 2s), 2.37 and 2.42(total 3H, 2s), 7.18–7.38(2H, m), 7.63–7.90(7H, m) |
| 5-71 | 1.32 and 1.33(total 9H, 2s), 2.31, 2.39, 2.42 and 2.59(total 6H, 4s), 7.12–7.87(9H, m) |
| 5-92 | 1.30 and 1.33(9H, 2s), 7.14–7.40, 7.66–7.90 and 7.98–8.04(total 9H, 3m) |
| 5-95 | 1.32(9H, s), 2.52(3H, s), 2.56(3H, s), 7.04(1H, bs), 7.23–7.48(4H, m) |
| 5-110 | 1.20–1.57(5H, m), 1.35(9H, s), 1.73–1.91(3H, m), 2.11–2.20(2H, m), 2.59(3H, s), 2.82–2.95 (1H, m), 7.03(1H, s), 7.28–7.50(4H, m) |

A few examples of compositions of the present invention are described below. Additives and addition ratios are not limited to those in the examples, and can be changed in a wide range. The "parts" used in the formulation examples are parts by weight.

EXAMPLE 2
Wettable Powder

| | |
|---|---|
| A compound of the present invention | 40 parts |
| Diatomaceous earth | 53 parts |
| Higher alcohol sulfate | 4 parts |
| Alkylnaphthalene sulfonate | 3 parts |

The above compounds were mixed uniformly and pulverized finely to give a wettable powder containing 40% of the active ingredient.

EXAMPLE 3
Emulsifiable Concentrate

| | |
|---|---|
| A compound of the present invention | 30 parts |
| Xylene | 33 parts |
| Dimethylformamide | 30 parts |
| Polyoxyethylene alkylallyl ether | 7 parts |

The above compounds were mixed and solved to give an emulsifiable concentrate containing 30% of the active ingredient.

EXAMPLE 4
Dust

| | |
|---|---|
| A compound of the present invention | 10 parts |
| Talc | 89 parts |
| Polyoxyethylene alkylallyl ether | 1 part |

The above compounds were mixed uniformly and pulverized finely to give a dust containing 10% of the active ingredient.

EXAMPLE 5
Granules

| | |
|---|---|
| A compound of the present invention | 5 parts |
| Clay | 73 parts |
| Bentonite | 20 parts |
| Sodium dioctylsulfosuccinate | 1 part |
| Sodium phosphate | 1 part |

The above compounds were sufficiently pulverized and mixed. Water was added to it to knead well, followed by granulation and drying to give granules containing 5% of the active ingredient.

EXAMPLE 6

Flowable Concentrate

| | |
|---|---|
| A compound of the present invention | 10 parts |
| Sodium lignin sulfonate | 4 parts |
| Sodium dodecylbenzenesulfonate | 1 part |
| Xanthane gum | 0.2 parts |
| Water | 84.8 parts |

The above compounds were mixed and wet pulverized until the granule size became smaller than 1 μ, to give a flowable concentrate containing 10% of the active ingredient.

Availability in Industry

Examples are shown below that formulations containing compounds of the present invention, which were prepared according to such ways as described above, were applied as agricultural and horticultural insecticides and acaricides.

Test Example 1

Effects on *Pseudaletia separata* Walker

According to the instructions of the wettable powder described in the above Example 2, a wettable powder was diluted with water to make the compound concentration 125 ppm. Corn leaves were immersed in the solution for 30 seconds, air-dried and placed in a Petri dish containing 5 third instar larvae of *Pseudaletia separata* Walker. The dish was covered with a glass lid and placed in a thermostatic chamber of temperature of 25° C. and relative humidity of 65%. Mortality was assessed 6 days after treatment. Each test was replicated twice.

The results show that the following compounds had mortality of 100%.

5-1, 5-2, 5-3, 5-4, 5-5, 5-6, 5-7, 5-8, 5-9, 5-10, 5-11, 5-12, 5-13, 5-15, 5-16, 5-17, 5-18, 5-20, 5-21, 5-22, 5-23, 5-24, 5-25, 5-26, 5-27, 5-28, 5-30, 5-31, 5-33, 5-34, 5-38, 5-39, 5-40, 5-41, 5-48, 5-49, 5-50, 5-51, 5-54, 5-56, 5-57, 5-58, 5-59, 5-60, 5-61, 5-62, 5-63, 5-64, 5-65, 5-66, 5-67, 5-68, 5-69, 5-74, 5-78, 5-80, 5-83, 5-84, 5-85, 5-86, 5-87, 5-88, 5-96, 5-97, 5-99, 5-100, 5-101, 5-102, 5-103, 5-104, 5-105, 5-106, 5-107, 5-108, 5-109 and 5-110.

Chlordimeform used as a control killed 40% of the larvae.

Test Example 2

Effects on *Aphis gossypii* Glover

Adults of *Aphis gossypii* Glover were inoculated on cucumber seedlings planted in a 10-cm (diameter) pot and 10 days old after the germination. On the following day the adult aphids were removed, According to the instructions of the emulsifiable concentrate described in the above Example 3, an emulsifiable concentrate was diluted with water to make a compound concentration 8 ppm. The diluted formulation was sprayed over the cucumber seedlings infested with hatched nymphs. The seedlings were placed in a thermostatic chamber of temperature of 25° C. and relative humidity of 65%. Mortality was assessed 6 days after treatment. Each test was replicated twice.

The results show that the following compounds had mortality of 100 %.

5-1, 5-3, 5-4, 5-5, 5-6, 5-7, 5-8, 5-10, 5-12, 5-13, 5-15, 5-16, 5-20, 5-24, 5-25, 5-26, 5-27, 5-28, 5-30, 5-31, 5-33, 5-38, 5-39, 5-40, 5-41, 5-44, 5-45, 5-49, 5-51, 5-52, 5-54, 5-55, 5-56, 5-57, 5-58, 5-60, 5-61, 5-62, 5-63, 5-64, 5-65, 5-68, 5-69, 5-71, 5-74, 5-76, 5-77, 5-78, 5-79, 5-80, 5-83, 5-84, 5-85, 5-86, 5-87, 5-88, 5-89, 5-90, 5-91, 5-96, 5-99, 5-100, 5-101, 5-102, 5-103, 5-104, 5-105, 5-106, 5-107, 5-108, 5-109 and 5-110.

The known compounds shown in the following and used as controls killed none of the nymphs.

Control Compound A

A compound disclosed in Japanese Patent Laid-open No. Sho 53-92769

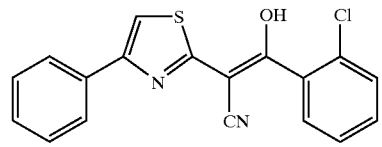

Control Compound B

A compound disclosed in Japanese Patent Laid-open No. Sho 55-154963

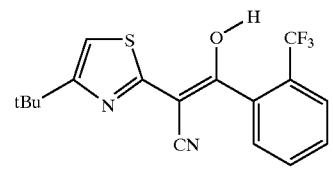

Control Compound C

A compound disclosed in EP 189960

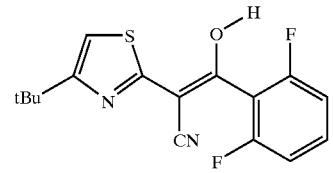

Control Compound D

A compound disclosed in Japanese Patent Laid-open No. Sho 55-154962

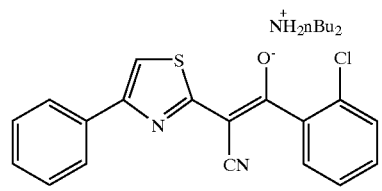

Control Compound E

A compound disclosed in Japanese Patent Laid-open No. Hei 10-298169 and WO 95/29591

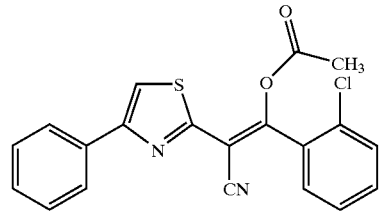

What is claimed is:

1. A compound represented by the formula (1)

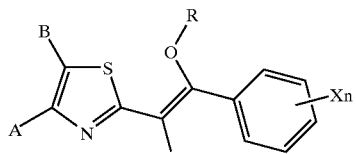
(1)

wherein

A is $C_{1-6}$ alkyl, $C_{3-6}$ cycloalkyl optionally substituted by halogen, $C_{1-6}$ alkyl, $C_{1-6}$ alkoxy or nitro, pyridyl optionally substituted by halogen, $C_{1-6}$ alkyl, $C_{1-6}$ alkoxy or nitro, thienyl optionally substituted by halogen, $C_{1-6}$ alkyl, $C_{1-6}$ alkoxy or nitro, or 2,6 di-substituted phenyl by halogen, $C_{1-6}$ alkyl, $C_{1-6}$ alkoxy or nitro;

B is hydrogen;

R is a group of Formula $COR^1$ (wherein $R^1$ is $C_{1-12}$ alkyl, $C_{1-6}$ haloalkyl, optionally substituted $C_{3-6}$ cycloalkyl, $C_{1-6}$ alkoxy, $C_{1-6}$ alkoxy $C_{1-6}$ alkyl, $C_{1-6}$ alkylthio $C_{1-6}$ alkyl, mono-$C_{1-6}$ alkylamino, di-$C_{1-6}$ alkylamino, optionally substituted phenyl $C_{1-6}$ alkyl, optionally substituted phenoxy $C_{1-6}$ alkyl, optionally substituted phenylthio $C_{1-6}$ alkyl or optionally substituted phenyl, or a group of Formula $SO_2R^2$ (wherein $R^2$ is $C_{1-6}$ alkyl or optionally substituted phenyl);

X is halogen, $C_{1-6}$ alkyl, $C_{1-6}$ haloalkyl, or $C_{1-6}$ alkoxy and at least one of the substituents is at position 2; and n is an integer between 1 and 5.

2. A pest controlling agent containing one or more compounds of Formula (1)

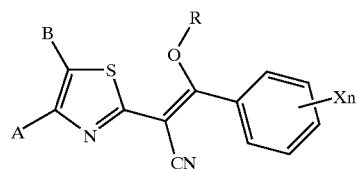
(1)

(wherein A, B, R, X and n are as defined above) as active ingredients.

* * * * *

UNITED STATES PATENT AND TRADEMARK OFFICE
CERTIFICATE OF CORRECTION

PATENT NO. : 6,492,404 B1  
DATED : December 10, 2002  
INVENTOR(S) : Yasushi Shibata et al.

Page 1 of 2

It is certified that error appears in the above-identified patent and that said Letters Patent is hereby corrected as shown below:

Column 5,  
Lines 1-10, replace:

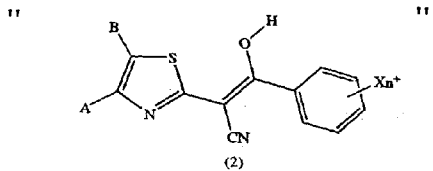

with:

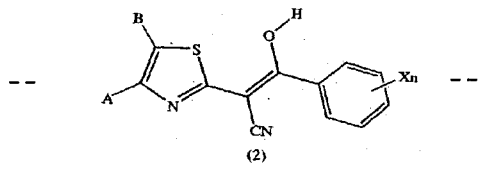

Column 23,  
Formula 5, replace:

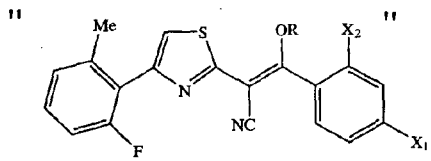

with:

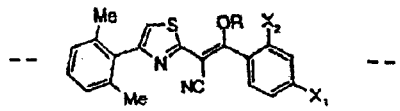

UNITED STATES PATENT AND TRADEMARK OFFICE
CERTIFICATE OF CORRECTION

PATENT NO. : 6,492,404 B1
DATED : December 10, 2002
INVENTOR(S) : Yasushi Shibata et al.

It is certified that error appears in the above-identified patent and that said Letters Patent is hereby corrected as shown below:

<u>Column 50,</u>
Line 43, replace "CL Br H CO2tBU" with -- CL Br H COtBU --

Column 68, Table 5, replace "5-9  2,6F2-PH  H  COtBU  2,6-F  [141-143.5]" with -- 5-9  2,6F2-PH  H  COtBU  2,6F2  [141-143.5] --

Column 69. Table 5, replace "5-48 2-CF2-PH H  COtBu  2-CF3  [146-147]" with -- 5-48 2-CF2-PH H COtBu  2-CF3  [146-148] --

Signed and Sealed this

Twenty-second Day of April, 2003

JAMES E. ROGAN
*Director of the United States Patent and Trademark Office*